(12) United States Patent
Barel et al.

(10) Patent No.: US 10,047,049 B2
(45) Date of Patent: Aug. 14, 2018

(54) PROCESS FOR PREPARING PRIDOPIDINE

(71) Applicants: Offir Barel, Kfar Saba (IL); Ramy Lidor-Hadas, Kvar-Sava (IL); Ronen Gottesfeld, Netanya (IL); Orel Yosef Mizrahi, Elad (IL); Anders Olof Ingemar Bergh, Karlskoga (SE); Ba-Vu Nguyen, Karlskoga (SE)

(72) Inventors: Offir Barel, Kfar Saba (IL); Ramy Lidor-Hadas, Kvar-Sava (IL); Ronen Gottesfeld, Netanya (IL); Orel Yosef Mizrahi, Elad (IL); Anders Olof Ingemar Bergh, Karlskoga (SE); Ba-Vu Nguyen, Karlskoga (SE)

(73) Assignee: TEVA PHARMACEUTICALS INTERNATIONAL GMBH, Jona (CH)

( * ) Notice: Subject to any disclaimer, the term of this patent is extended or adjusted under 35 U.S.C. 154(b) by 0 days.

(21) Appl. No.: 15/217,683

(22) Filed: Jul. 22, 2016

(65) Prior Publication Data
US 2017/0022158 A1    Jan. 26, 2017

Related U.S. Application Data

(60) Provisional application No. 62/195,756, filed on Jul. 22, 2015.

(51) Int. Cl.
C07D 211/24    (2006.01)
(52) U.S. Cl.
CPC ........ C07D 211/24 (2013.01); *C07B 2200/13* (2013.01)
(58) Field of Classification Search
None
See application file for complete search history.

(56) References Cited

U.S. PATENT DOCUMENTS

| | | | |
|---|---|---|---|
| 5,462,947 A | 10/1995 | Andersson et al. | |
| 6,924,374 B2 | 8/2005 | Sonesson et al. | |
| 7,417,043 B2 | 8/2008 | Sonesson et al. | |
| 7,923,459 B2 * | 4/2011 | Gauthier | C07D 211/24 514/317 |
| 9,006,445 B2 | 4/2015 | Sonesson et al. | |
| 9,012,476 B2 | 4/2015 | Zimmermann | |
| 9,139,525 B2 | 9/2015 | Wikström | |
| RE46,117 E | 8/2016 | Sonesson et al. | |
| 2007/0238878 A1 | 10/2007 | Desmond et al. | |
| 2013/0267552 A1 | 10/2013 | Waters et al. | |
| 2015/0202302 A1 | 7/2015 | Licht et al. | |
| 2015/0209344 A1 | 7/2015 | Zimmermann et al. | |
| 2015/0209346 A1 | 7/2015 | Hayden | |
| 2015/0216850 A1 | 8/2015 | Hayden | |
| 2015/0374677 A1 | 12/2015 | Schmidt et al. | |
| 2016/0095847 A1 | 4/2016 | Sonesson | |
| 2016/0166559 A1 | 6/2016 | Sonesson | |
| 2016/0176821 A1 | 6/2016 | Wu et al. | |
| 2016/0243098 A1 | 8/2016 | Geva et al. | |
| 2017/0020854 A1 | 1/2017 | Licht et al. | |
| 2017/0266170 A1 | 9/2017 | Waters et al. | |

FOREIGN PATENT DOCUMENTS

| | | |
|---|---|---|
| WO | WO 1999/003470 | 1/1999 |
| WO | WO 01/46145 A1 * | 6/2001 |
| WO | WO 2011/107583 | 9/2011 |
| WO | WO 2016/138135 | 9/2016 |
| WO | PCT/US2017/19266 | 8/2017 |

OTHER PUBLICATIONS

International Preliminary Report on Patentability for PCT International Application No. PCT/EP05/011020 (WO 2006/040155) published Apr. 20, 2006 (Gauthier et al.).
Written Opinion of the International Search Authority for PCT International Application No. PCT/EP05/011020 (WO 2006/040155) published Apr. 20, 2006 (Gauthier et al.).
Feb. 22, 2007 International Preliminary Report on Patentability and Written Opinion of the International Search Authority for PCT International Application No. No. PCT/EP05/011020 (WO 2006/040155) published Apr. 20, 2006 (Gauthier et al.).
International Search Report for PCT International Application No. PCT/US2016/043682 (WO 2017/015609) published Jan. 26, 2017 (Barel et al.).
Written Opinion of the International Search Authority for PCT International Application No. PCT/US2016/043682 (WO 2017/015609) published Jan. 26, 2017 (Barel et al.).
Sep. 26, 2008 Office Action in connection with U.S. Appl. No. 11/733,512.
Dec. 23, 2008 Response to Sep. 26, 2008 Office Action in connection with U.S. Appl. No. 11/733,512.
Mar. 12, 2009 Office Action in connection with U.S. Appl. No. 11/733,512.
Jun. 9, 2009 Response to Mar. 12, 2009 Office Action in connection U.S. Appl. No. 11/733,512.
Aug. 24, 2009 Office Action in connection with U.S. Appl. No. 11/733,512.
Oct. 5, 2009 Response to Aug. 24, 2009 Office Action in connection with U.S. Appl. No. 11/733,512.
Nov. 17, 2009 Office Action in connection with U.S. Appl. No. 11/733,512.
Feb. 17, 2010 Response to Nov. 17, 2009 Office Action in connection with U.S. Appl. No. 11/733,512.
Declaration filed Aug. 13, 2010 in connection with U.S. Appl. No. 11/733,512.
Aug. 18, 2010 Office Action in connection with U.S. Appl. No. 11/733,512.
Nov. 12, 2010 Response to Aug. 18, 2010 Office Action in connection with U.S. Appl. No. 11/733,512.
Apr. 26, 2006 letter to European Patent Office from the A. Carlsson Research AB, applicant of PCT International Application No. PCT/EP2005/011020.

(Continued)

*Primary Examiner* — Zinna Northington Davis
(74) *Attorney, Agent, or Firm* — John P. White; Cooper & Dunham LLP

(57) ABSTRACT

This invention provides a pridopidine base in a solid form, a method of preparing the solid pridopidine base, and a composition comprising the pridopidine base including a pharmaceutical composition.

24 Claims, No Drawings

(56) References Cited

OTHER PUBLICATIONS

Nov. 29, 2010 Office Action issued by the Australian Patent Office in connection with Australian Patent Application No. 2005293754.
Jun. 28, 2011 Response to Nov. 29, 2010 Office Action filed in connection with Australian Patent Application No. 2005293754.
Mar. 1, 2012 Office Action issued by the Canadian Patent Office in connection with Canadian Patent Application No. 2584831.
Aug. 28, 2012 Response to Mar. 1, 2012 Office Action filed in connection with Canadian Patent Application No. 2584831.
May 22, 2009 First Office Action issued by the Chinese Patent Office in connection with Chinese Patent Application No. 200580038591.0 (with English Language translation).
Dec. 7, 2009 Response to May 22, 2009 First Office Action issued by the Chinese Patent Office in connection with Chinese Patent Application No. 200580038591.0.
Jan. 8, 2010 Second Office Action issued by the Chinese Patent Office in connection with Chinese Patent Application No. 200580038591.0 (with English Language translation).
May 25, 2010 Response to Jan. 8, 2010 Second Office Action issued by the Chinese Patent Office in connection with Chinese Patent Application No. 200580038591.0.
Jul. 14, 2010 Third Office Action issued by the Chinese Patent Office in connection with Chinese Patent Application No. 200580038591.0 (with English Language translation).
Oct. 29, 2010 Response to Jul. 14, 2010 Third Office Action issued by the Chinese Patent Office in connection with Chinese Patent Application No. 200580038591.0.
Mar. 5, 2012 Office Action issued in connection with Indian Patent Application No. 3481/DELNP/2007.
May 2, 2013 Response to Office Action dated Mar. 5, 2012 in connection with Indian Patent Application No. 3481/DELNP/2007.
Mar. 10, 2011 Office Action issued by the Mexican Patent Office in connection with Mexican Patent Application No. MX/a/2007/004215.
Apr. 26, 2011 Response to Mar. 10, 2011 Office Action issued by the Mexican Patent Office in connection with Mexican Patent Application No. MX/a/2007/004215.
Sep. 19, 2012 Office Action issued by the South Korean Intellectual Property Office in connection with South Korean Patent Application No. 2007-7010900.
Mar. 13, 2013 Response to Sep. 19, 2012 Office Action issued by the South Korean Intellectual Property Office in connection with South Korean Patent Application No. 2007-7010900.
Dec. 3, 2012 Office Action issued in connection with European Patent Application No. 05793645.2.
Apr. 12, 2013 Response to Office Action dated Dec. 3, 2012 in connection with European Patent Application No. 05793645.2.
Jun. 6, 2014 Office Action issued in connection with European Patent Application No. 05793645.2.
Dec. 16, 2014 Response to Office Action dated Jun. 6, 2014 in connection with European Patent Application No. 05793645.2.
Jul. 14, 2015 Office Action issued in connection with European Patent Application No. 05793645.2.
Nov. 20, 2015 Response to Office Action dated Jul. 14, 2015 in connection with European Patent Application No. 05793645.2.
"A multiple-ascending dose study of pridopidine in healthy volunteers." Trial Profile, Adis Insight, Springer, Latest Information Update: May 28, 2012 (Table of Contents), http://adisinsight.springer.com/trials/700207057.
NeuroSearch, "NeuroSearch A/S reports conclusions from the Multiple Ascending Dose study (MAD) with Huntexil®", May 28, 2012.
Dyhring T, Nielsen EØ, Sonesson C, Pettersson F, Karlsson J, Svensson P, Christophersen P, Waters N., The dopaminergic stabilizers pridopidine (ACR16) and (−)-OSU6162 display dopamine D(2) receptor antagonism and fast receptor dissociation properties. Eur J Pharmacol. Feb. 25, 2010;628(1-3):19-26.
Huntington Study Group HART Investigators, "A Randomized, Double-Blind, Placebo-Controlled Trial of Pridopidine in Huntington's Disease" Movement Disorders, vol. 28, No. 10, 2013.
Johansson, Birgitta et al., Placebo-controlled cross-over study of the monoaminergic stabiliser (−)-OSU6162 in mental fatigue following stroke or traumatic brain injury, Acta Neuropsychiatrica / vol. 24 / Issue 05 / Oct. 2012, pp. 266-274.
Michl, Martin et al. "Pridopidine in the pharmacological treatment of Huntington's disease", Clin. Invest. (2013) 3(7), 691-699.
Rung, Johan P., et al. The dopaminergic stabilizers (−)-OSU6162 and ACR16 reverse (+)-MK-801-induced social withdrawal in rats. Prog Neuropsychopharmacol Biol Psychiatry. Jun. 2005; 29(5):833-9.
Sahlholm K, Århem P, Fuxe K, Marcellino D., The dopamine stabilizers ACR16 and (−)-OSU6162 display nanomolar affinities at the σ-1 receptor. Mol Psychiatry. Jan. 2013;18(1):12-4.
Tedroff J, Ekesbo A, Sonesson C, Waters N, Carlsson A., Long-lasting improvement following (−)-OSU6162 in a patient with Huntington's disease. Neurology. Oct. 22, 1999; 53(7):1605-6.

* cited by examiner

PROCESS FOR PREPARING PRIDOPIDINE

This application claims priority of U.S. Provisional Application No. 62/195,756, filed Jul. 22, 2015, the entire contents of which are hereby incorporated by reference herein.

Throughout this application, certain publications are referenced in parentheses. Full citations for these publications are presented in a References section immediately before the claims. Disclosures of the publications cited in the References section are hereby incorporated by reference in their entireties into this application in order to more fully describe the state of the art as of the date of the invention described herein.

BACKGROUND OF INVENTION

Pridopidine (Huntexil®) is a unique compound developed for the treatment of patients with motor symptoms associated with Huntington's disease. The chemical name of pridopidine is 4-(3-(Methylsulfonyl)phenyl)-1-propylpiperidine, and its Chemical Registry Number is CAS 346688-38-8 (CSID:7971505, 2016). The Chemical Registry number of pridopidine hydrochloride is 882737-42-0 (CSID: 25948790 2016). Processes of synthesis of pridopidine and a pharmaceutically acceptable salt thereof are disclosed in U.S. Pat. No. 7,923,459. U.S. Pat. No. 6,903,120 claims pridopidine for the treatment of Parkinson's disease, dyskinesias, dystonias, Tourette's disease, iatrogenic and non-iatrogenic psychoses and hallucinoses, mood and anxiety disorders, sleep disorder, autism spectrum disorder, ADHD, Huntington's disease, age-related cognitive impairment, and disorders related to alcohol abuse and narcotic substance abuse.

US Patent Application Publication Nos. 20140378508 and 20150202302, describe methods of treatment with high doses of pridopidine and modified release formulations of pridopidine, respectively.

BRIEF SUMMARY OF THE INVENTION

This invention provides a pridopidine base in a solid form.

This invention also provides a composition comprising pridopidine base.

This invention also provides a composition comprising pridopidine base, wherein the composition is free of isopropyl alcohol.

In some embodiments, the composition is free of chloride or free of pridopidine hydrochloride.

This invention also provides a pharmaceutical composition comprising pridopidine base.

This invention also provides a process for preparing solid pridopidine base comprising
  a) obtaining a solution comprising pridopidine base, and
  b) precipitating pridopidine base from the solution to form solid pridopidine base.

This invention also provides a process for preparing pridopidine hydrochloride from pridopidine free base comprising
  a) obtaining solid pridopidine free base,
  b) dissolving solid pridopidine free base in an alcohol to form a solution,
  c) filtering the solution, and
  d) adding to the solution a mixture of hydrochloric acid and an alcohol which is the same as the alcohol in which the pridopidine base is dissolved in step (b) to precipitate pridopidine hydrochloride.

This invention also provides isolated pridopidine base prepared by the process of the invention.

The invention also provides a composition comprising Compound 9, wherein the composition is free of 3-bromothioanisole.

The invention also provides a composition comprising Compound 9, wherein the composition is free of THF, chloride, hexylbromide, 1-chlorobutanol, or thioanisol.

The invention also provides a composition comprising Compound 9, wherein the composition is free of chloride.

The invention also provides a composition comprising Compound 8, wherein the amount of Compound 11 present in the composition is less than 0.30% by weight or less than 0.15% by weight.

The invention also provides, a composition comprising pridopidine HCl, wherein the amount of Compound 4 present in the composition is less than 0.15% by weight or less than 0.10% by weight.

The invention also provides, a composition comprising Compound 9, wherein the amount of Compound 12 present in the composition is less than 0.30% by weight.

The invention also provides, a composition comprising pridopidine HCl, wherein the amount of Compound 13 present in the composition is less than 0.15% by weight.

DETAILED DESCRIPTION OF THE INVENTION

The present invention is based in part on the identification of a method to synthesize solid pridopidine base that can be used per se or converted to a salt for use as a drug substance.

The known process for the synthesis of pridopidine HCl is flawed in that it requires, inter alia, harsh conditions including extreme temperatures (e.g. lithiation at less than −35° C. and elimination at 110° C.), distillation and extractions. The present disclosure provides, inter alia, an optimized process for the synthesis of solid form of pridopidine base, which can be used per se or converted to a salt, including pridopidine HCl.

This invention provides a pridopidine base in a solid form.

This invention also provides a composition comprising pridopidine base.

This invention also provides a composition comprising pridopidine base, wherein the composition is free of isopropyl alcohol.

In an embodiment, the composition is free of chloride or free of pridopidine hydrochloride.

This invention also provides a pharmaceutical composition comprising pridopidine base. In some embodiments the pharmaceutical composition is free of isopropyl alcohol. In some embodiments, the pharmaceutical composition is free of chloride or free of pridopidine hydrochloride.

This invention also provides a process for preparing solid pridopidine base comprising
  a) obtaining a solution comprising pridopidine base, and
  b) precipitating pridopidine base from the solution to form solid pridopidine base.

In an embodiment, the process further comprises precipitating pridopidine base with a volume of one or more alkanes.

In an embodiment, the alkane is n-heptane.

In an embodiment, the solution comprises one or more organic solvents or water, or a mixture thereof.

In an embodiment, the solution is a mixture of toluene and water.

In an embodiment, the process further comprises adding a strong base to the solution.

In an embodiment, the strong base is NaOH.

In an embodiment, the strong base is added until the pH of the solution is pH 8-14, pH 11-14 or about pH 13.

In an embodiment, the solution comprises an aqueous layer and an organic layer, and the process further comprises separating the organic layer from the aqueous layer and washing the organic layer with water.

In an embodiment, the step of washing the organic layer with water removes Compound 1 from the organic layer.

In an embodiment, the process further comprises forming the pridopidine base with a chemical purity in which the weight percent of Compound 1 is less than 0.2% or less than 0.15% of the total amounts of pridopidine base and Compound 4.

In an embodiment, the process further comprises removing an amount of the organic solvent under vacuum distillation to obtain a mixture comprising a volume of the organic solvent.

In an embodiment, the process further comprises precipitating pridopidine base after the vacuum distillation.

In an embodiment, the process further comprises forming the pridopidine base.

In an embodiment, the ratio of the volume of organic solvent to the volume of one or more alkanes during the step of precipitating the pridopidine base is between 1:1.3 to 1:3 or about 1:2.

In an embodiment, the process further comprises a catalytic reduction of Compound 8

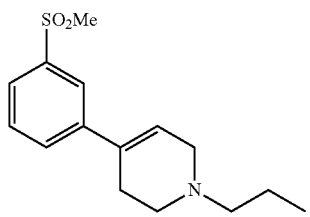

Compound 8 at a predetermined reduction temperature and with an amount of a reduction catalyst to form pridopidine base.

In an embodiment, the reduction catalyst is a palladium catalyst, a platinum catalyst, a ruthenium catalyst, or a palladium on carbon catalyst.

In an embodiment, the catalyst is a palladium catalyst, preferably a JM type 402 catalyst.

In an embodiment, the catalyst is a JM type 402 catalyst.

In an embodiment, the amount of the reduction catalyst is present in an amount of 5%-20% w/w, 5%-15% w/w, 5%-12% w/w, 8%-10% w/w, about 10% w/w or about 8% w/w. In an embodiment, the catalytic reduction is complete in 0.1-20 hours, 0.1-10 hours, 0.1-5 hours, 0.5-5 hours, 0.5-1 hour or about 50 minutes.

In an embodiment, the predetermined reduction temperature is 5-60° C., 30-50° C., 40-50° C., 36-50° C. or about 40° C.

In an embodiment, the predetermined reduction temperature is 0-39° C., 0-35° C., 0-30° C., 10-30° C., or 20-30° C.

In an embodiment, the pridopidine base formed is free of pridopidinium.

In an embodiment, the catalyst is a JM type 402 catalyst and the amount of the JM type 402 catalyst present in the reaction is 8%-10% w/w.

In an embodiment, the reaction is complete after 0.1-2 hours, 0.1-1 hours, about 1 hour or about 50 minutes.

In an embodiment, the process further comprises dissolving Compound 8 in water.

In an embodiment, the process further comprises comprising mixing Compound 8 with a weak acid.

In an embodiment, the weak acid is formic acid.

In an embodiment, the process further comprises cold addition to prevent the formation of pridopidinium.

In an embodiment, the process further comprises oxidizing the sulfide of Compound 10:

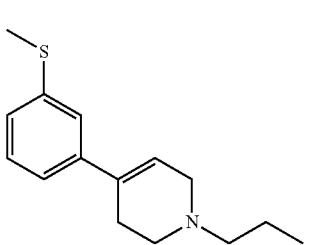

Compound 10 with a catalytic oxidizing agent and an oxidant; to give Compound 8:

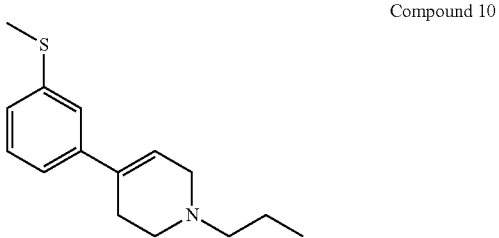 [SMILES: CCCN1CC=C(c2cccc(SC)c2)CC1]

Compound 8

Compound 10 may in the form shown above or it may instead be in the form shown in Table 1.

In an embodiment, the step of oxidizing the sulfide of Compound 10 is conducted at a temperature of 40-60° C., 35-38° C. or 35-55° C. In some embodiment, the temperature is about 45° C.

In an embodiment, the catalytic oxidizing agent is a tungsten oxidizing agent.

In an embodiment, the tungsten oxidizing agent is sodium tungstate.

In an embodiment, the oxidant is a peroxide.

In an embodiment, the peroxide is sodium peroxide.

In an embodiment, the process further comprises adding the oxidant in two batches in a first batch and a second batch.

In an embodiment, the process further comprises adding one batch of oxidant, followed by adding the second batch after the accumulated heat is released.

In an embodiment, the Compound 8 formed is free of Compound 1.

In an embodiment, the process further comprises dehydrating Compound 9:

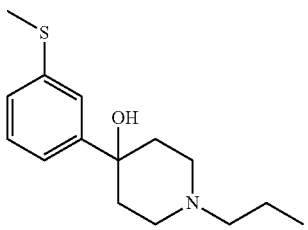

Compound 9 with a strong acid for an amount of time and at a temperature; to give Compound 10 or a solution comprising Compound 10. In some embodiments, the yield of the step of dehydrating Compound 9 is 20-95%, 50-95%, or 50-95%.

In an embodiment, the amount of strong acid is 1.0-4.5 equivalents, 1.8-4.0 equivalents, 1.8-3.0 equivalents, 1.8-2.5 equivalents, or about 1.0-2.0 equivalents.

In an embodiment, the amount of time is 1-22 hours, 2-5 hours, or about 3.5 hours. In an embodiment, the temperature is below 118° C., below 90° C., below 83° C., below 80° C., below 70° C., 57° C.-80° C., or about 70° C.

In an embodiment, the strong acid is sulfuric acid.

In an embodiment, the dehydration of Compound 9 with a strong acid is conducted in a solvent selected from toluene, xylene and hexanes.

In an embodiment, Compound 10 is extracted from a solution comprising Compound 10 using water and without the use of NaOH.

In an embodiment, the chemical purity of Compound 10 is 90-99.4%, 95-99.4%, 98.9-99.7%, or 98.9-99.4%. In another embodiment, the yield of the step of dehydrating Compound 9 is 20-95%, 50-95%, or 50-95%.

In an embodiment, the process further comprises lithiating 3-bromothioanisole with a lithiating agent using a continuous flow reactor to obtain 3-lithium thioanisole.

In an embodiment, the continuous flow reactor comprises a solvent and wherein the solvent is tetrahydrofuran (THF).

In an embodiment, lithiation of 3-bromothioanisole has an average residence time of 1-60 seconds, 2.8-14 seconds, 7-14 seconds, 4-10 seconds, or about 5.6 seconds.

In an embodiment, the process further comprises performing a coupling reaction between 3-lithium thioanisole and 1-propyl-4-piperidone to form Compound 9 or a solution comprising Compound 9 using a continuous flow reactor. In an embodiment, the coupling has an average residence time of 8-480 seconds, 10-480 seconds, 8-15 seconds, or about 8 seconds.

In an embodiment, the lithiation of 3-bromothioanisole and/or the coupling is performed at a temperature of between 15° C. and −100° C., between −5° C. and −100° C., between −40° C. and −100° C., between −60° C. and −100° C., between −60° C. and −80° C., between −80° C. to −100° C., between 15° C. and −25° C., between 15° C. and −10° C., between 5° C. and −5° C., between 0° C. and 10° C., between 2° C. and 8° C., about 0° C. or about −5° C.

In an embodiment, the amount of equivalents of the lithiating agent used is between 0.97 and 1.20. In an embodiment, the lithiating agent is an alkyllithium. In an embodiment, the alkyllithium is Hex-Li.

In an embodiment, the process further comprises precipitating Compound 9 from the solution to form solid Compound 9.

In an embodiment, the process further comprises quenching the solution comprising Compound 9 with water to form a solution comprising Compound 9.

In an embodiment, the process further comprises adding toluene to the solution comprising Compound 9 and washing with water.

In an embodiment, the process further comprises distilling a solution comprising Compound 9 by vacuum distillation.

In an embodiment, Compound 9 formed has a chemical purity with a THF level of 2-150 ppm, 2-100 ppm, 5-90 ppm, 7-84 ppm, 7-79 ppm, or 7-23 ppm.

In an embodiment, Compound 9 is precipitated with an alkane selected from pentane, hexane, heptane, and octane.

In an embodiment, the alkane is heptane. In an embodiment, the precipitation of Compound 9 is completed at a temperature of between −70° C. and 10° C., between −70° C. and 0° C., between −70° C. and −5° C., between −30° C. and 0° C., or about −5° C.

In an embodiment, the Compound 9 formed is free of Compound 16.

In an embodiment, the process further comprises lithiating 3-bromothioanisole with a lithiating agent followed by performing a coupling between 3-lithium thioanisole and 1-propyl-4-piperidone to form the hydrochloride salt of Compound 9 or a solution comprising the hydrochloride salt of Compound 9 and using a vacuum distillation to obtain a composition comprising the hydrochloride salt of Compound 9 wherein the composition comprises less than 1% w/w, less than 0.9% w/w or less than 0.5% w/w of THF.

The invention further provides a process of lithiating 3-bromothioanisole with a lithiating agent followed by performing a coupling between 3-lithium thioanisole and 1-propyl-4-piperidone to form the hydrochloride salt of Compound 9 or a solution comprising the hydrochloride salt of Compound 9 and using a vacuum distillation to obtain a composition comprising the hydrochloride salt of Compound 9 wherein the composition comprises less than 1% w/w, less than 0.9% w/w or less than 0.5% w/w of THF.

In an embodiment, the composition comprising the hydrochloride salt of Compound 9 has an assay purity above 90%, above 95%, or 100%.

In an embodiment, the composition comprising Compound 9 has a chemical purity of more than 99.5%, more than 99%, more than 95%, or more than 90%.

In an embodiment, the process further comprises simultaneously adding the 3-bromothioanisole and the lithiating agent to a suitable solvent.

In an embodiment, the process further comprises adding 3-bromothioanisole to a solution of a lithiating agent in a suitable solvent wherein the temperature is maintained at less than −70° C. or less than −60° C.

In an embodiment, the suitable solvent is THF and wherein the THF is maintained at a temperature of less than −70° C., or less than −60° C.

In an embodiment, the solution comprising the hydrochloride salt of Compound 9 or the solid hydrochloride of Compound 9 is free of THF or THF remainders. In an embodiment, the the hydrochloride salt of Compound 9 or the solid hydrochloride of Compound 9 is free of residual THF.

This invention also provides a process for preparing pridopidine hydrochloride from pridopidine free base comprising
  a) obtaining solid pridopidine free base,
  b) dissolving solid pridopidine free base in an alcohol to form a solution,
  c) filtering the solution, and
  d) adding to the solution a mixture of hydrochloric acid and an alcohol which is the same as the alcohol in which the pridopidine base is dissolved in step (b) to precipitate pridopidine hydrochloride.

In an embodiment, the alcohol is isopropyl alcohol (IPA).

In an embodiment, the pridopidine hydrochloride formed is free of Compound 4 or has less than 0.01% by weight, less than 0.07% by weight, or less than 0.05% by weight of Compound 4.

This invention also provides an isolated solid form of pridopidine free base prepared by the process disclosed herein.

In another embodiment, provided is Compound 9 having an assay of more than 88%, more than 90%, more than 92%, more than 94%, more than 96% or about 96-97% Further provided is Compound 9 having a chemical purity of more than 99.0%

The invention also provides a composition comprising Compound 9, wherein the composition is free of 3-bromothioanisole.

The invention also provides a composition comprising Compound 9, wherein the composition is free of THF, chloride, hexylbromide; 1-chlorobutanol; or thioanisol.

The invention also provides a composition comprising Compound 9, wherein the composition is free of chloride.

The invention also provides a composition comprising Compound 8, wherein the amount of Compound 11 present in the composition is less than 0.30% by weight or less than 0.15% by weight.

The invention also provides a composition comprising pridopidine HCl, wherein the amount of Compound 4 present in the composition is less than 0.15% by weight or less than 0.10% by weight.

The invention also provides a composition comprising Compound 9, wherein the amount of Compound 12 present in the composition is less than 0.30% by weight.

In certain embodiments, Compound 9 is in it hydrochloride salt form.

The invention also provides, a composition comprising pridopidine HCl, wherein the amount of Compound 13 present in the composition is less than 0.15% by weight.

In an embodiment, the pridopidine HCl is further crystallized. In some embodiments, the crystallization is performed in a mixture of IPA/HCl.

This invention further provides pridopidine hydrochloride formed by the process disclosed herein.

The present invention contemplates each individual step of the invention or each individual embodiment of the invention without another step of the process. As an example, the subject invention includes a process of dehydrating Compound 9 with a strong acid for an amount of time and at a temperature, to give Compound 10; the invention separately contemplates a solution comprising Compound 10.

For the foregoing embodiments, each embodiment disclosed herein is contemplated as being applicable to each of the other disclosed embodiments. In addition, the elements recited in pharmaceutical composition embodiments can be used in the method and use embodiments described herein.

Pharmaceutically Acceptable Salts

The active compounds for use according to the invention may be provided in any form suitable for the intended administration. Suitable forms include pharmaceutically (i.e. physiologically) acceptable salts, and pre- or prodrug forms of the compound of the invention.

Examples of pharmaceutically acceptable addition salts include, without limitation, the non-toxic inorganic and organic acid addition salts such as the hydrochloride, the hydrobromide, the nitrate, the perchlorate, the phosphate, the sulphate, the formate, the acetate, the aconate, the ascorbate, the benzenesulphonate, the benzoate, the cinnamate, the citrate, the embonate, the enantate, the fumarate, the glutamate, the glycolate, the lactate, the maleate, the malonate, the mandelate, the methane-sulphonate, the naphthalene-2-sulphonate, the phthalate, the salicylate, the sorbate, the stearate, the succinate, the tartrate, the toluene-p-sulphonate, and the like. Such salts may be formed by procedures well known and described in the art.

Pharmaceutical Compositions

While the compounds for use according to the invention may be administered in the form of the raw compound, it is preferred to introduce the active ingredients, optionally in the form of physiologically acceptable salts, in a pharmaceutical composition together with one or more adjuvants, excipients, carriers, buffers, diluents, and/or other customary pharmaceutical auxiliaries.

In an embodiment, the invention provides pharmaceutical compositions comprising the active compounds or pharmaceutically acceptable salts or derivatives thereof, together with one or more pharmaceutically acceptable carriers therefore, and, optionally, other therapeutic and/or prophylactic ingredients know and used in the art. The carrier(s) must be "acceptable" in the sense of being compatible with the other ingredients of the formulation and not harmful to the recipient thereof.

The pharmaceutical composition of the invention may be administered by any convenient route, which suits the desired therapy. Preferred routes of administration include oral administration, in particular in tablet, in capsule, in dragé, in powder, or in liquid form, and parenteral administration, in particular cutaneous, subcutaneous, intramuscular, or intravenous injection. The pharmaceutical composition of the invention can be manufactured by the skilled person by use of standard methods and conventional techniques appropriate to the desired formulation. When desired, compositions adapted to give sustained release of the active ingredient may be employed.

Further details on techniques for formulation and administration may be found in the latest edition of *Remington's Pharmaceutical Sciences* (Mack Publishing Co., Easton, Pa.).

As used herein, "effective" as in an amount effective to achieve an end means the quantity of a component that is sufficient to yield an indicated therapeutic response without undue adverse side effects (such as toxicity, irritation, or allergic response) commensurate with a reasonable benefit/risk ratio when used in the manner of this disclosure. For example, an amount effective to treat a movement disorder. The specific effective amount varies with such factors as the particular condition being treated, the physical condition of the patient, the type of mammal being treated, the duration of the treatment, the nature of concurrent therapy (if any), and the specific formulations employed and the structure of the compounds or its derivatives.

As used herein, an amount of pridopidine as measured in milligrams refers to the milligrams of pridopidine (4-[3-

(methylsulfonyl)phenyl]-1-propyl-piperidine) present in a preparation, regardless of the form of the preparation. For example, a unit dose containing "90 mg pridopidine" means the amount of pridopidine in a preparation is 90 mg, regardless of the form of the preparation. Thus, when in the form of a salt, e.g. pridopidine hydrochloride, the weight of the salt form necessary to provide a As used herein, to "treat" or "treating" encompasses, e.g., reducing a symptom, inducing inhibition, regression, or stasis of the disorder and/or disease. As used herein, "inhibition" of disease progression or disease complication in a subject means preventing or reducing the disease progression and/or disease complication in the subject.

As used herein, a composition that is "free" of a chemical entity means that the composition contains, if at all, an amount of the chemical entity which cannot be avoided. In another embodiment, a composition that is free of a chemical entity contains less than 5% of the chemical entity, by weight. In a further embodiment, a composition that is free of a chemical entity contains less than 1% of the chemical entity, by weight. In another embodiment, a composition that is free of a chemical entity contains less than 0.5% of the chemical entity, by weight. In an additional embodiment, a composition that is free of a chemical entity contains less than 0.1% of the chemical entity, by weight. In a further embodiment, a composition that is free of a chemical entity contains 0.0% of the chemical entity, by weight.

Certain embodiments of the invention make use of continuous flow reactors, some of which are commercially available, such as Corning® AdvancedFlow™ Reactors (including Corning® AdvancedFlow™ LF Reactor, Corning® AdvancedFlow™ G1 Reactor).

In the present application, reference to the amount of an impurity in a product should be understood to mean that the product is actually a composition comprising the product and the impurity. For example, when reference is made to the amount of Compound 11 in Compound 8, this should be understood to mean that a composition comprises Compound 8 and the amount of Compound 11.

The following abbreviations are used throughout this application:

3BTA (3-Bromothioanisole); 3LTA (3-Lithium thioanisole); AcN (Acetonitrile); BrT (3BTA); cGMP (Current Good Manufacturing Practice); cryst (Crystallized); DS (Drug substance); eq (Equivalent/s); exp. (Experiment/s); FB (free base); GL (Glass line); GVS (Gravimetric vapor sorption); HAZOP (Hazard and operability study); hr/hrs (hour/hours); IPA (iso-propanol); IPC (In-process control); KF (Karl Fischer); LOD (Loss on drying); LT (Less than); MeOH (Methanol); Me-THF (Methyl THF); Min (Minute/s); ML (mother liquor); MT (More than); MTBE (Methyl tert-butyl ether); ND (Not determined); NLT (not less than); NM (Not measured); NMP (N-Methyl-2-pyrrolidone); NMT (not more than); QL (Quantification Limit); PTFE (Polytetrafluoroethylene); ref. (Reference); RM/s (Raw material/s); rpm (round per minute); r.t. (room temperature); RT (Retention time); RRT (Relative retention time); Sec (Second); SS (Steady state); TA (thioanisole); Tr (reaction temperature); Temp (Temperature); THF (Tetrahydrofuran); Tol (Toluene); and Vol (Volume/s).

Table 1 shows the chemical structures of various Compounds disclosed herein.

TABLE 1

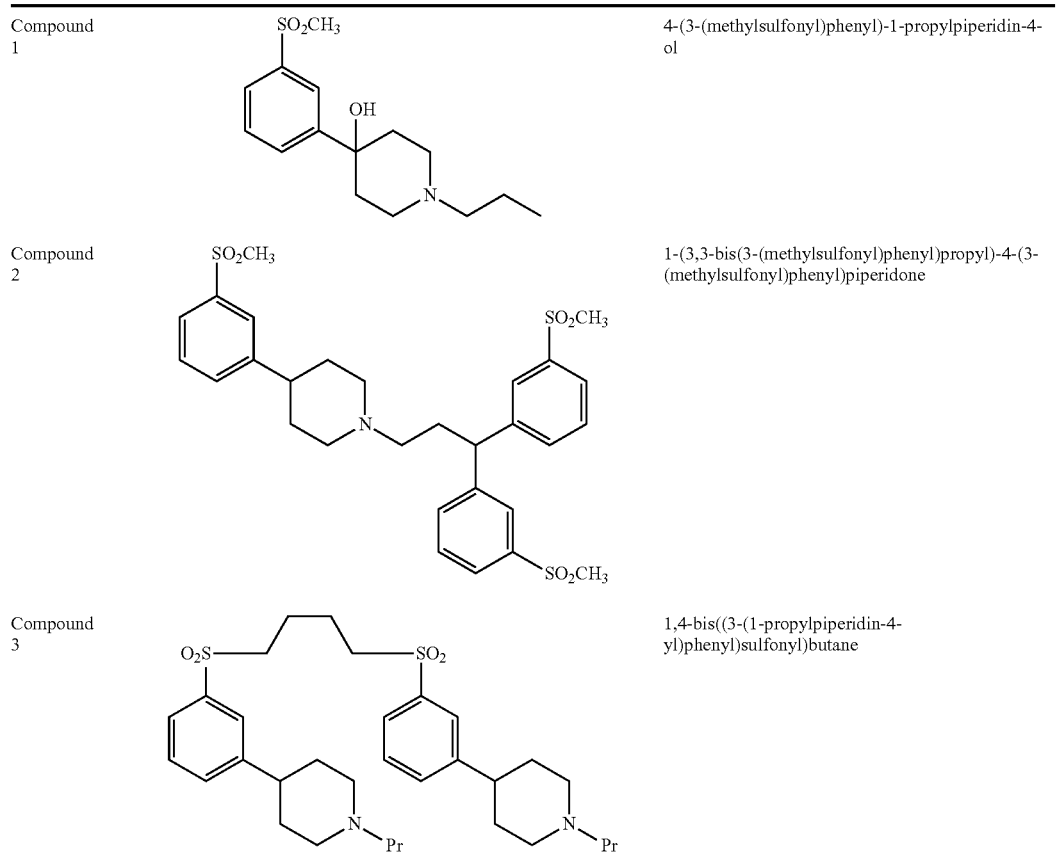

| Compound 1 | [structure] | 4-(3-(methylsulfonyl)phenyl)-1-propylpiperidin-4-ol |
| Compound 2 | [structure] | 1-(3,3-bis(3-(methylsulfonyl)phenyl)propyl)-4-(3-(methylsulfonyl)phenyl)piperidone |
| Compound 3 | [structure] | 1,4-bis((3-(1-propylpiperidin-4-yl)phenyl)sulfonyl)butane |

TABLE 1-continued

| | | |
|---|---|---|
| Compound 4 | 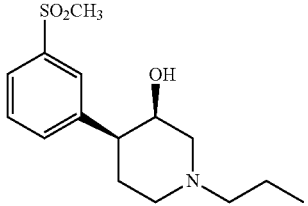 [SMILES: CCCN1CC[C@@H](c2cccc(S(C)(=O)=O)c2)[C@@H](O)C1] | (3R,4S)-4-(3-(methylsulfonyl)phenyl)-1-propylpiperidin-3-ol |
| Compound 5 | 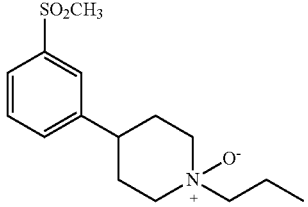 | 4-(3-(methylsulfonyl)phenyl)-1-propylpiperidine-1-oxide |
| Compound 6 | 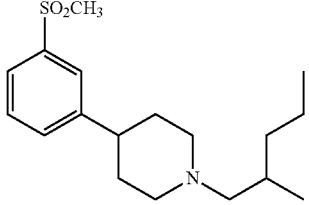 [SMILES: CCCC(C)CN1CCC(c2cccc(S(C)(=O)=O)c2)CC1] | 1-(2-methylpentyl)-4-(3-(methylsulfonyl)phenyl)piperidine |
| Compound 7 | 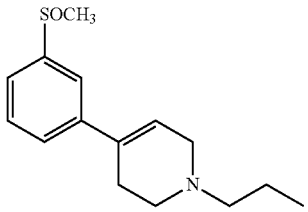 | 4-(3-(methylsulfinyl)phenyl)-1-propyl-1,2,3,6-tetrahydropyridine |
| Compound 8 | 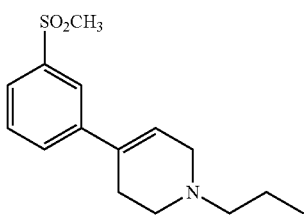 [SMILES: CCCN1CC=C(c2cccc(S(C)(=O)=O)c2)CC1] | 4-(3-(methylsulfonyl)phenyl)-1-propyl-1,2,3,6-tetrahydropyridine |
| Compound 9 | 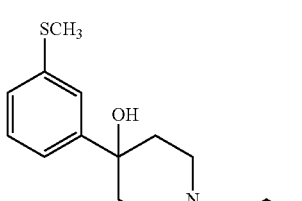 | 4-(3-(methylthio)phenyl)-1-propylpiperidin-4-ol |
| Compound 10 | 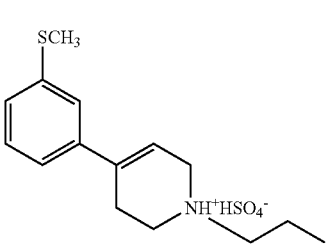 | 4-(3-(methylthio)phenyl)-1-propyl-1,2,3,6-tetrahydropyridin-1-ium hydrogen sulfate |

TABLE 1-continued

| | | |
|---|---|---|
| Compound 11 | | 1,4-bis((3-(1-propyl-1,2,3,6-tetrahydropyridin-4-yl)phenyl)sulfonyl)butane |
| Compound 12 | | 4-(3-((3-(methylthio)phenyl)thio)phenyl)-1-propylpiperidin-4-ol |
| Compound 13 | | 4-(3-((3-(methysulfonyl)phenyl)sulfonyl)phenyl)-1-propylpiperidine |
| Compound 14 | | 4-(3-((3-(methylsulfonyl)phenyl)sulfonyl)phenyl)-1-propyl-1,2,3,6-tetrahydropyridine |
| Compound 15 | | 4-(3-(methylsulfonyl)phenyl)-1-propylpyridin-1-ium formate |
| Compound 16 | | 4-(3-(methylthio)phenyl)-1,1'-dipropyl-[3,4'-bipiperidine]-4,4'-diol |
| Pyridopidinium | | 4-(3-(methylsulfonyl)phenyl)-1-propylpyridin-1-ium |

EXAMPLES

Example 1: Pridopidine-HCl Synthesis

An initial process for synthesizing pridopidine HCl shown in Scheme 1 and is a modification of the process disclosed in U.S. Pat. No. 7,923,459.

The synthesis of Compound 9 started with the halogen-lithium exchange of 3-bromothioanisole (3BTA) in THF employing n-hexyllithium (HexLi) in hexane as the lithium source. Li-thioanisole (3LTA) intermediate thus formed was coupled with 1-propyl-4-piperidone (1P4P) forming a Li-Compound 9. These two reactions require low (cryogenic) temperature. The quenching of Li-Compound 9 was done in water/HCl/MTBE resulting in precipitation of Compound 9-HCl salt. A cryogenic batch mode process for this step was developed and optimized. The 3BTA and THF were cooled to less than −70° C. A solution of HexLi in n-hexane (33%) was added at a temperature below −70° C. and the reaction is stirred for more than 1 hour. An in-process control sample was taken and analyzed for completion of halogen exchange. 1-propyl-4-piperidone (1P4P) was then added to the reaction at about −70° C. letting the reaction mixture to reach −40° C. and further stirred at this temperature for about 1 hour. An in-process sample was analyzed to monitor the conversion according to the acceptance criteria (Compound 9 not less than 83% purity). The reaction mixture was added to a mixture of 5N hydrochloric acid (HCl) and methyl tert-butyl ether (MTBE). The resulting precipitate was filtered and washed with MTBE to give the hydrochloric salt of Compound 9 (Compound 9-HCl) wet.

Batch mode technique for step 1 requires an expensive and high energy-consuming cryogenic system that cools the reactor with a methanol heat exchange, in which the methanol is circulated in counter current liquid nitrogen. This process also brings about additional problems originated from the work-up procedure. The work-up starts when the reaction mixture is added into a mixture of MTBE and aqueous HCl. This gives three phases: (1) an organic phase that contains the organic solvents MTBE, THF and hexane along with other organic related materials such as thioanisole (TA), hexyl-bromide, 3-hexylthioanisole and other organic side reaction impurities (2) an aqueous phase containing inorganic salts (LiOH and LiBr), and (3) a solid phase which is mostly Compound 9-HCl but also remainders of 1P4P as an HCl salt.

The isolation of Compound 9-HCl from the three phase work-up mixture is by filtration followed by MTBE washings. A major problem with this work-up is the difficulty of the filtration which resulted in a long filtration and washing operations. The time it takes to complete a centrifugation and washing cycle is by far beyond the normal duration of such a manufacturing operation. The second problem is the inevitable low and non-reproducible assay (purity of ~90% on dry basis) of Compound 9-HCl due to the residues of the other two phases. It should be noted that a high assay is important in the next step in order to control the amount of reagents. The third problem is the existence of THF in the wet Compound 9-HCl salt which is responsible for the Compound 3 impurity that is discussed below.

Scheme 1:

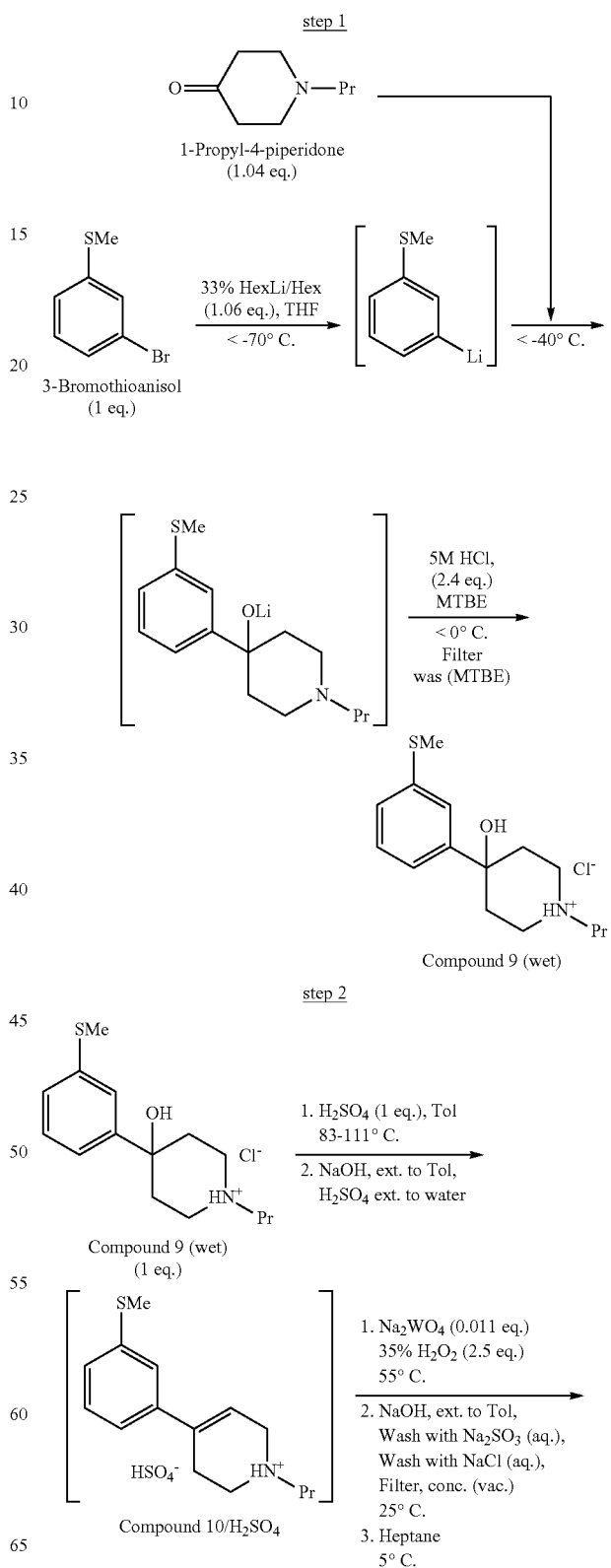

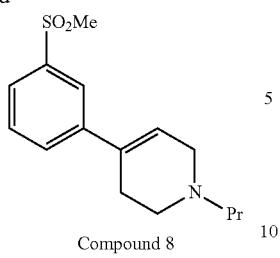

Compound 8

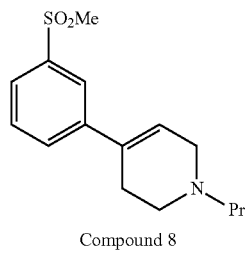

Compound 8 step 3

1. Water,
   HCO₂H (5.0 eq.)
   10% Pd/C (0.15 weight eq.)
   30° C.
2. Filter, wash (water)
   NaOH, ext IPA/Tol,
   sovent change to IPA
3. 2 M HCl
   5° C.

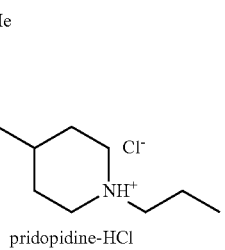

pridopidine-HCl

Therefore, a few of the deficiencies of the synthesis of solid pridopidine free base that need to be addressed to include:

1. Cryogenic Technology: In the first step of Scheme 1, the process is performed in a very low temperature (−70° C. to −80° C.) and as a traditional batch mode production. The lower the temperature, the higher the yield of the first intermediate (Compound 9-HCl). These conditions require a cryogenic system, which is expensive and consumes a large amount of energy.

2. Assay of Compound 9-HCl: Quenching the reaction mixture of step 1 of scheme 1 in aqueous HCl/MTBE solution gives a solid intermediate, Compound 9-HCl, is filtered as is. The resulting wet Compound 9-HCl with relative low assay (about 85-95% on a dry basis). The assay obtained in this process was always very different from its chromatographic purity which is 98-99%. In addition, since high assay is important for the calculation of reagents quantities needed for the next stage (Compound 8), a work-up that provides a higher assay is needed.

3. Residual THF: THF residues are responsible for Compound 3 impurity in the final pridopidine-HCl product. THF should be removed before the next stage of the elimination reaction.

4. Filtration difficulties in step 1: Filtration and washing of Compound 9-HCl obtained after the quenching is very difficult and consequently requires a much longer centrifugation time in production. This is a major process-related problem for this stage. There is a need to shorten filtration and washings for this stage.

5. Purification of impurities that accompanied step 1: hexylbromide, 4-chlorobutanol, 3BTA and thioanisole should be removed.

6. Degradation during the elimination reaction, step 2 (Compound 8): The elimination takes a substantial amount of time because it is done in atmospheric azeotropic distillation. This distillation requires a long heating step to reach the high distillation temperature (111-118° C.) and to remove all eliminated water. This distillation also has a long cooling time. During the high temperature distillation of water, a step used to obtain intermediate Compound 10, both Compound 9-HCl and Compound 10 are partly decomposed which resulted in reduced yield of isolated Compound 9-HCl. Different conditions are needed to decrease temperature and perform the elimination reaction.

7. Better control on the addition of hydrogen peroxide:

8. Restrictive Compound 1 release specification in step H (Compound 8): The maximum allowed amount of Compound 1 impurity in Compound 8 is small (less than 0.05%) to ensure that the next steps will be successful. The reason for this is because step 3 of scheme 1 is not capable of purifying Compound 1. As a result, the conversion of Compound 9-HCl to Compound 10 should be efficient since any traces of Compound 9-HCl will give Compound 1 impurity after the oxidation process. The process of scheme 1 achieved this goal by boiling the reaction mixture for a long time to ensure that a very high conversion of Compound 9 (more than 99.9%) is obtained. An improved process is needed.

9. High amount of Pd/C catalyst in step 3: The Pd/C catalyst is the most expensive reagent in the process. There are also environmental concerns associated with the Pd/C catalyst. During step 3 the amount of Pd/C used is 0.15% w/w. There is a need to reduce the amount of this catalyst used.

10. Optimize the extractions of step 2 and 3: In step 2 & 3 of Scheme 1 there is a large number of extractions, some of which are for solvent swaps and changing from a salt to a free base while others are for work-up. Preferably, the number of the extractions should be minimized.

11. Solvents swap at step 3: After the reduction and during the work-up of pridopidine there are 2 solvents exchanging (water to toluene and toluene to IPA). The last solvent swap with IPA was performed by 3 IPC monitored repeated distillations which adversely affect the yield. It is desirable to minimize those solvents swaps and to simplify this step.

12. Improving the yield of the pridopidine crude step.

13. Isolation of solid pridopidine free base: To control the physical properties of the pridopidine-HCl.

14. Adding a crystallization step: In process shown in Scheme 1, pridopidine-HCl is precipitated in IPA by HCl/IPA addition rather than by crystallization. This process gives no control on the particle size distribution (PSD) of pridopidine-HCl. The resulted fine solid, makes dry blend formulation difficult to accomplish and forms lumps during storage. A crystallization process should be developed to give better control on the physical properties of pridopidine-HCl.

Example 2
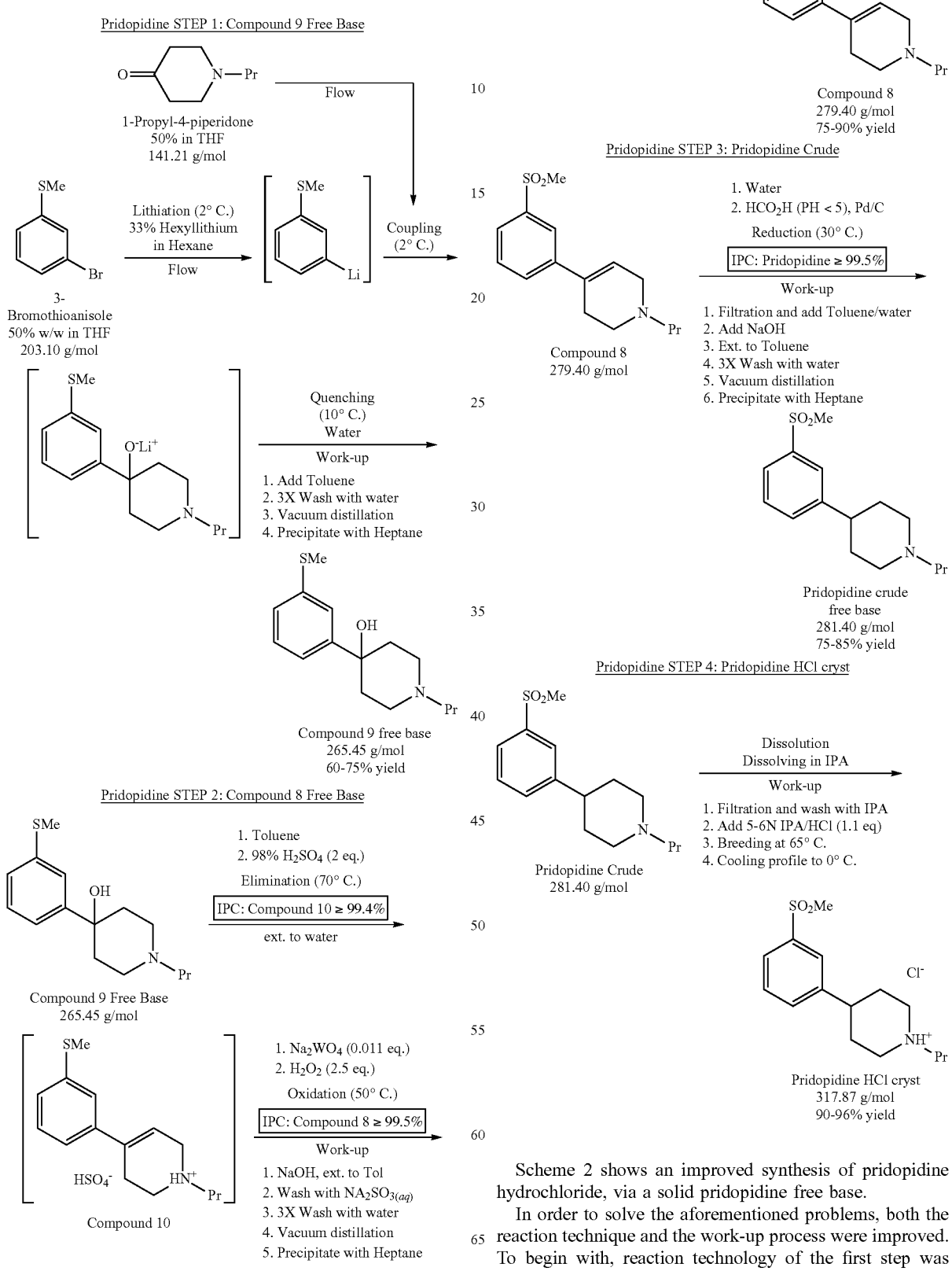
Scheme 2 shows an improved synthesis of pridopidine hydrochloride, via a solid pridopidine free base.
In order to solve the aforementioned problems, both the reaction technique and the work-up process were improved. To begin with, reaction technology of the first step was switched from batch to flow which allows much higher working temperatures (−20° C. to 5° C.) and obviates the need for a cryogenic system and dedicated infrastructure. During this flow technology adaptation, the THF amount was optimized. In addition, a work-up was developed of which Compound 9-FB (free base rather than HCl salt) having an assay higher than 98% and chemical purity (CP) higher than 99% was isolated. These changes did not affect the yield obtained in the process of Example 1 (60-75% on a dry basis).

The following examples discuss in more detail the process shown in Example 2.

Example 3: Summary of Compound 9 Preparation (Step 1 of Scheme 2)

Compound 9 was prepared following the synthesis hereinbelow:

A solution of 50% w/w 3-bromothioanisole (3-BTA) in THF extra dry (<0.05% water) which is then flowed and cooled to 1-2° C. (Q3BTA=61.0 g/min, Q3BTA>30 g/min, Tj<2° C.). Filtered solution of 30% w/w hexyllithium in n-hexane is flowed in parallel and cooled to 1-2° C. (Tj<2° C., QLi=46.5 g/min QLi=0.76 Q3BTA±5%, 1.11 eq±5%). The two streams are mixed together to form 3LTA at Tr=5-9° C. (exothermic), when the residence time is 6 s (residence time=4-8 s, Tr=(−30)–10° C.). The 3LTA immediately mixes with cooled filtered solution of 50% w/w 1P4P in THF extra dry (Tj<2° C., 1.06 eq±5%, Q1P4P=45.0 g/min, Q1P4P=0.73Q3BTA+5% g/min) to form lithiated-Compound 9 when the residence time is 9 s (residence time>5 s, Tr=(−30)–10° C., P=1.5-15 bar). The lithiated-Compound 9 solution is quenched by flowing into a reactor containing 5 Vol of water at 5° C. (Tr<30° C.), forming a solid Compound 9 FB. A washing cycle is done every 40-45 min. The washing cycle includes 1-1.5 mm solvent flowing wash (THF/n-hexane), then washing with water for 8-10 min and finally washing again with solvents (THF/n-hexane) for 1-1.5 min. When the flow reaction is over, 5 Vol of toluene are added into the reactor. The reaction mixture is warmed up to 40° C. in order to dissolve the solid Compound 9 FB into the organic phase. The two phases are mixed together at 40° C. (Tr=35-50° C., pH=12-14) for 30 min, the mixing is stopped to allow phase separation and after 20 min the lower aqueous cloudy phase is removed (first extraction). Four Vol of fresh water are added and mixed for 20 min, keeping the temperature at 40° C. (Tr=35-50° C., pH=11-13). The mixing is stopped to allow the phases to separate, giving a clear aqueous phase which is removed after 15 min (second extraction). Four (4) Vol of fresh water are added and mixed for 20 min at 40° C. (Tr=35-50° C., pH<10). The mixing is stopped for 15 min and the lower, clear aqueous phase is removed (last extraction). The reaction mixture is cooled down to Tr<15° C. and distilled in vacuum in two stages. In warmed to 25° C. and the stirring is on high speed to break bubbles. After most of the THF has been distilled (~½ Vol in the distillate), the Tj is warmed up to 40-60° C. and the P<90 mbar until 2-3 Vol remain in the reactor. One (1) Vol of n-heptane is added at 35-45° C. and the slurry that was formed is dissolved by warming up to 50-60° C. When a clear solution is obtained the mixture is cooled down to 40-50° C. for crystallization. The mixture is mixed at 40-50° C. for not less than (NLT) 4 h (breeding time). The slurry is cooled down over 4 h to −5° C. and mixed for not less than 4 h. Three (3) Vol of n-heptane are added to the slurry and mixed for an additional 1 h. The solid is filtered, washed with 2 Vol n-heptane and dried under vacuum (P<50 mbar) at 40° C. to constant weight. Dried Compound 9 FB is obtained as a yellowish to white solid, with 50%-70% yield.

In this example and in other examples, a Vol of a solvent is the number of volumes of the specific solvent compared to the referenced solvent.

Example 3.1: Applying Flow Reaction Technology to Compound 9 Preparation

The use of a flow reaction for halogen-lithium exchange followed by an addition reaction with ketone brings about safety, stability and economic benefits. The use of a flow system is almost scale independent and provides flexibility for the manufacturer.

Using a continuous flow reactor has the following benefits in relation to this particular preparation for Compound 9:

1. the risk of a runaway occurring because of the two fast and exothermic reactions is reduced compared with a batch reaction mode, and
2. a continuous flow reactor eliminates the need for cryogenic technology which is expensive and requires a lot of energy and infrastructure compared to a batch reaction mode.

After laboratory experiments mimicking flow reaction conditions it was concluded that flow reaction setting for step 1 is not only possible but it can be also favorable since it enables a fast reaction at a relatively high temperature. It was also demonstrated that Hex-Li equivalents can be varied from 1.04 to 1.10.

Flow Reaction System

The feasibility of the two Compound 9 reactions in a continuous reactor system was determined based on laboratory studies. A Corning® AdvancedFlow™ reactor system was chosen for this purpose. The two reactions were carried out in flow plate shape reactors while the quenching and the following work-up continued in a batch process mode. The system construction materials are either glass or ceramic and have high chemical resistance to the reagents.

Feasibility of Compound 9 Reactions Using Flow System

The flow reactor was cooled to −52° C. which caused precipitation of 3LTA. Thus, the bath temperature was limited to more than −30° C. In the same reaction except for a higher temperature, cooling (−22° C.) 3LTA did not precipitate. The configuration was set to mix the 3LTA flow with the 1P4P flow as quickly as possible and eliminate dead volumes. Several tests were performed using 50% THF solution of each SM using the work-up from Example 1 (MTBE/HCl precipitation) for isolation. Table 2 shows data of step 1 of the pridopidine HCl synthesis from Scheme 2.

TABLE 2

Compound 9 preparation using flow reaction

| Exp. No. | $T_{bath}$ | Flow set of 3BTA | Residence times [reaction I/II] | Conversion IPC$_2$ [% Compound 9] | [% 3BTA] | CP | Assay | Yield |
|---|---|---|---|---|---|---|---|---|
| 701 | −22° C. | 20 ml/min | 14 sec/54 sec | 84.1% | <0.05% | 99.9% | 77.5% | 63% |
| 702 | −22° C. | 36 ml/min | 8 sec/33 sec | 88.8% | <0.05% | 99.9% | 78.6% | 59% |
| 703 | −7° C. | 40 ml/min | 7 sec/29 sec | 87.9% | <0.05% | 99.8% | 74.2% | 60% |

These tests provided good purity and assay results. Chemical purity (CP) is above 99% and neither TA nor 3BTA are identified in Compound 9-HCl as in the method disclosed in Example 1. The assay is between 70-80% purity, which are the usual values for dry Compound 9-HCl obtained by the procedure of Example 1. The yield is between 55-70% and is still a subject to further improvement (the yield of the cryogenic reference batch test was 67%).

The flow process is feasible at both −7° C. and −22° C. bath temperatures and provides similar results regardless of residence times.

Table 3 shows data from experiments where $T_{bath}$=−7° C. and −22° C. $T_1$ represents the jacket temperature at 3BTA inlet stream before it reacts with HexLi. $T_2$ represents the outlet jacket temperature of the halogen-lithium exchange reaction plate. $T_3$ represents the outlet jacket temperature at the coupling reaction's 1$^{st}$ plate and T4 at the 2$^{nd}$ plate outlet.

TABLE 3

Compound 9, second set of experiments using 3 pump flow reaction configuration with flow meters

| Exp. No. | Temp. (SS) | Pumps A, B, and C actual flows | Residence times [reaction I/II] | Conversion [% Compound 9] | Purity | Yield (based on assay) |
|---|---|---|---|---|---|---|
| 801 | $T_{bath}$ = −22° C.<br>$T_1$ = −18.7° C.<br>$T_2$ = −17.6° C.<br>$T_3$ = −12.5° C.<br>$T_4$ = −20.9° C. | A = 27.4 g/min (1.17 eq)<br>B = 34.5 g/min<br>C = 25.1 g/min (1.05 eq) | 8 sec/23 sec | 86.9% | CP = 99.4%<br>Assay = 75.2% | 64% |
| 802 | $T_{bath}$ = −22° C.<br>$T_1$ = −18.2° C.<br>$T_2$ = −17.9° C.<br>$T_3$ = −12.7° C.<br>$T_4$ = −19.5° C. | A = 26.5 g/min (1.17 eq)<br>B = 33.1 g/min<br>C = 25.6 g/min (1.11 eq) | 8.4 sec/11.8 sec | 86.4% | CP = 99.6%<br>Assay = 76.1% | 64% |
| 803 | $T_{bath}$ = −7° C.<br>$T_1$ = −3.0° C.<br>$T_2$ = −1.2° C.<br>$T_3$ = 2.5° C.<br>$T_4$ = −3.7° C. | A = 35 g/min (1.34 eq)<br>B = 38 g/min<br>C = 25.5 g/min (1.04 eq) | 6.8 sec/10.1 sec | 69.5% | CP = 96.7%<br>Assay = 54.5% | 70% |
| 804 | $T_{bath}$ = −7° C.<br>$T_1$ = −3.4° C.<br>$T_2$ = −1.7° C.<br>$T_3$ = 3.2° C.<br>$T_4$ = −4.0° C. | A = 30 g/min (1.23 eq)<br>B = 35.5/min<br>C = 28.4 g/min (1.15 eq) | 7.6 sec/10.7 sec | 76.9% | CP = 99.1%<br>Assay = 52.0% | 66% |

The results in Table 3 show that reducing the coupling reaction's residence time had no effect on both yield and chemical purity (Experiment Nos. 801 and 802). In both cases $T_4$ is similar to $T_3$ which indicates that the configuration with half residence time in reaction II is sufficient enough to remove the heat generated in this reaction. The results in Table 3 also show that when $T_{bath}$ was raised to −7° C. there was no practical effect on performance. The results in Table 3 further demonstrate the use of higher equivalents of HexLi results in a lower conversion and a lower assay; however a higher yield (based on assay) occurred. It is assumed that excess of HexLi gives more side reactions that apparently lower the assay and increase TA side product.

Therefore, producing Compound 9 in a flow system is feasible.

Parameters for Flow Reaction

Compound 9-FB was isolated according to the present developed work-up (Example 2). Table 4 shows data from flow reaction experiments in a continuous reactor system.

TABLE 4

Compound 9: third set of experiments

| Exp. No. | Temp. | Flows | Residence times [sec] | Conversion [% Compound 9] | Purity | Yield |
|---|---|---|---|---|---|---|
| 902 | $T_{bath}$ = −7° C.<br>$T_1$ = −5.7° C.<br>$T_2$ = −1.2° C.<br>$T_3$ = −5.6° C.<br>$T_4$ = −5.7° C. | HexLi = 27.4 g/min<br>(1.1 eq)<br>3BTA = 36 g/min<br>1P4P = 26 g/min | 8.4/12.0 | 77.9% | CP = 99.0%<br>Assay = 101.4% | 70.0% |
| 903 | $T_{bath}$ = −7° C.<br>$T_1$ = 0.7° C.<br>$T_2$ = 6.0° C.<br>$T_3$ = 0.8° C.<br>$T_4$ = 0.8° C. | HexLi = 41 g/min<br>(1.1 eq)<br>3BTA = 54 g/min<br>1P4P = 39 g/min | 5.6/7.9 | 76.7% | CP = 98.7%<br>Assay = 101.2% | 73.0% |
| 904 | $T_{bath}$ = −2° C.<br>$T_1$ = −1.0° C.<br>$T_2$ = 5.1° C.<br>$T_3$ = −0.8° C.<br>$T_4$ = −1.1° C. | HexLi = 40.5 g/min<br>(1.1 eq)<br>3BTA = 54 g/min<br>1P4P = 38.7 g/min | 5.6/8.0 | 79.5% | CP = 97.5%<br>Assay = 93.7% | 75.0% |
| 905 | $T_{bath}$ = −2° C.<br>$T_1$ = −0.9° C.<br>$T_2$ = 6.1° C.<br>$T_3$ = −0.7° C.<br>$T_4$ = −0.7° C. | HexLi = 54 g/min<br>(1.0 eq)<br>3BTA = 79 g/min<br>1P4P = 57 g/min | 4.0/5.7 | 82.6% | CP = 97.1%<br>Assay = 93.2% | 70.0% |
| 906 | $T_{bath}$ = 1° C.<br>$T_1$ = 0.5° C.<br>$T_2$ = 6.4° C.<br>$T_3$ = 1.1° C.<br>$T_4$ = 0.8° C. | HexLi = 40.5 g/min<br>(1.1 eq)<br>3BTA = 54 g/min<br>1P4P = 39 g/min | 5.6/8.0 | 78.1% | CP = 99.1%<br>Assay = 96.9% | 70.0% |
| 907 | $T_{bath}$ = 2° C.<br>$T_1$ = 2.8° C.<br>$T_2$ = 7.8° C.<br>$T_3$ = 2.9° C.<br>$T_4$ = 2.6° C. | HexLi = 40 g/min<br>(1.1 eq)<br>Bromo = 54 g/min<br>Piperidone = 39 g/min | 5.6/8.0 | 79.7% | CP = 98.9%<br>Assay = 96.4% | 74% |

The data in Table 4 indicates that there is no correlation between the relatively low assay (<95%) obtained in Experiment Nos. 904 and 905 to the temperature (in Experiment Nos. 906 and 907 bath temperature is higher) and residence time. It is likely that the low assay resulted from insufficient temperature control during distillation in the work-up. In Experiment Nos. 907 and 906 the chemical purity and the assay were higher. The residence time lower limit of halogen-lithium exchange reaction can be lowered to 4 sec (Experiment No. 905) or even 2.8 sec (Experiment No. 901). The residence time lower limit of the coupling reaction can be lowered to 8.0 sec with no effect on yield or assay. It can likely be lowered even to 5.7 sec (Experiment No. 905). Bath temperature can be raised to 2° C. (exothermic reaction gave 7.8° C. near halogen-lithium exchange reaction outlet) with no effect on purity. The yields are consistently above 70%, which is similar to cryogenic reaction mode.

To summarize, the working range of Compound 9 flow reaction in a continuous reactor system (G1 system) was determined in the set of experiments detailed above. Residence time of the halogen-lithium exchange reaction should be 2.8-14 sec, preferably 5.6 sec and residence time of coupling reaction should be not less than 8 sec. Experiment No. 906 was defined as a representative batch that provides 1.9 kg Compound 9 in 51 minutes with a 70% yield and 96.8% assay.

Example 3.2: Compound 9 Work-Up

The Compound 9-HCl wet cake formed at the end of step 1 of Example 1 has a poor solid filterability. The improved work-up solves the filtration difficulty using isolation and controlled crystallization rather than precipitation of Compound 9-HCl. In addition, the work-up should raise the assay which is relatively low, and more importantly, not consistent.

Precipitation of Compound 9 as a Free Base

Toluene and n-heptane were used for Compound 9-FB work-up. First, Compound 9-HCl was put in water/toluene followed by splitting with NaOH. The water phase was discarded and n-heptane was added to the toluene phase as an anti-solvent for the precipitation of Compound 9-FB.

Table 5 shows data from the precipitation of Compound 9.

TABLE 5

Precipitation of Compound 9-FB in toluene/n-heptane system

| Exp. No. | Dissolution in toluene | Toluene/n-heptane precipitation mixture[1] | Filtration | Assay | CP | Yield |
|---|---|---|---|---|---|---|
| 1201 | 5 Vol | 4 Vol/7 Vol | Smooth (LT 1 min) | 97.0% | 99.9% | 65% |
| 1202 | 2 Vol | 2 Vol/0 Vol | Smooth (LT 1 min) | 99.0% | 99.9% | 61% |
| 1203 | 2.5 Vol | 2 Vol/0 Vol | Smooth (LT 1 min) | 99.1% | 99.8% | 60% |
| 1204 | 2.5 Vol | 2 Vol/2.5 Vol | Smooth (LT 1 min) | 99.6% | 99.8% | 93% |

[1]After partial removal of toluene by vacuum evaporation

The data presented in Table 5 shows the advantages of toluene/n-heptane precipitation system for Compound 9-FB isolation. In this system, the filtration is easy and the Compound 9 assay is significantly improved. The raw material for these experiments was low assay (72-82%) dry Compound 9-HCl and the experiment produced the desired compound with assays above 97%. The assay was dramatically raised due to the extractions with water after the addition of NaOH. Moreover, n-heptane acts as an anti-solvent which helped to raise also the yield. With the right toluene/n-heptane ratio (Experiment Nos. 1204 and 1203) a good yield can be achieved. The mass balance of Experiment No. 1204 was 98% when 5% of the product is in the M.L and less than 2% lost in the mechanic loss (mainly reactor wall). During the extraction no product was identified in the aqueous phases. The filtration temperature was −5° C.

Table 6 provides data from the precipitation step.

TABLE 6

Producing Compound 9-FB with present work-up

| Exp. No. | Dissolution in toluene | Toluene/n-heptane precipitation mixture[1] | Filtration | Assay | CP | Yield |
|---|---|---|---|---|---|---|
| 1301 | 3 Vol | 3 Vol/3 Vol | Smooth (LT 1 min) | 98.3% | 99.3% | 53% |
| 1202 | 5 Vol | 3 Vol/3 Vol | Smooth (LT 1 min) | 97.8% | 99.3% | 62% |

TABLE 6-continued

Producing Compound 9-FB with present work-up

| Exp. No. | Dissolution in toluene | Toluene/n-heptane precipitation mixture[1] | Filtration | Assay | CP | Yield |
|---|---|---|---|---|---|---|
| 1302 | 5 Vol | 3 Vol/2 Vol | Smooth (LT 1 min) | 98.4% | 99.4% | 60% |
| 1303 | 5 Vol | 2.5 Vol/3 Vol | Smooth (LT 1 min) | 96.7% | 99.0% | 67% |
| 1304 | 5 Vol | 2.5 Vol/5.5 Vol | Smooth (LT 1 min) | 97.3% | 99.1% | 68% |
| 1305 | 5 Vol | 2.5 Vol/5.5 Vol | Smooth (LT 1 min) | 98.2% | 99.3% | 70% |
| 1306 | 5 Vol | 2.5 Vol/4.2 Vol | Smooth (LT 1 min) | 97.8% | 99.2% | 68% |

[1]After partial removal of toluene by vacuum evaporation

The data in Table 6 shows that Compound 9-FB precipitation provides a product with a higher purity than the Compound 9-HCl precipitation shown in Example 1. All the assay results are more than 96.5% and the CP is not less than 99.0%. The filtrations were performed without difficulties in all toluene/n-heptane ratios. Yields were between 68-70% using the correct conditions. Thus, it is recommended to use about 5 Vol of toluene for the extraction and wash the organic mixture with about 3×5 Vol of water until pH≤10. Water extractions remove the lithium salts (LiBr and LiOH) and partly remove THF. Vacuum distillation was added in order to reduce the volumes of toluene. After reaching about 2.5 Vol of reaction mixture, 2.5 Vol of n-heptane are added. In this case the precipitation gave heavy, non-stirrable slurry.

The slurry was dissolved by warming and crystallized by gradual cooling. In order to dissolve Compound 9-FB in toluene/n-heptane mixture the reaction mixture was warmed with enriched toluene mixture (2.5 Vol/1 Vol). The reaction mixture was then cooled to −5° C. during which crystallization started. In order to enhance crystallization and increase yield, three additional volumes of n-heptane were added 1 hr before filtration. A narrow range for the assay was set because the next stage requires precise equivalents of sulfuric acid. It was thus decided to set assay specification to not less than 95%.

Purification Capability of the Present Work-Up

This present work-up includes extractions, vacuum distillation and cooling profile. Table 7 shows the levels of 3BTA in the present work-up.

TABLE 7

3BTA level in Compound 9-FB

| | Conversion (IPC$_1$) | | 3BTA | | |
|---|---|---|---|---|---|
| Exp. No. | [% TA] | [% 3BTA] | in Compound 9 | Assay | Yield |
| 1401 | 70.5% | 29.5% | LT 0.06% | 97.4% | 52% |
| 1402 | 83.4% | 16.6% | LT 0.06% | 98.8% | 52% |
| 1403 | 84.9% | 15.1% | LT 0.06% | 97.8% | 68% |
| 1302 | 96.9% | 3.1% | LT 0.06% | 98.4% | 60% |

Table 7 shows the efficiency of the purification of 3BTA by the present work-up (Scheme 2). If the reaction mixture contains high level of 3BTA (accompanied with low yield due to incomplete lithiation) the work-up is capable to purify up to 30% 3BTA. This observation makes IPC1 unnecessary to maintain quality.

Other impurities that can be identified in Compound 9-FB are hexyl bromide and TA. Hexyl bromide is a liquid organic side product formed during the lithiation reaction. TA is formed from 3LTA that had not reacted with 1P4P and underwent quenching with water. Since the present work-up is based on isolating Compound 9-FB from the organic phase and both hexyl bromide and TA are organic compounds, their purification is important during the work-up (Table 8).

TABLE 8

TA & hexyl bromide levels throughout the work-up stages (Experiment No. 1302)

| Stage | TA [% area] | Hexyl bromide [% area] | Chromatographic purity of Compound 9 |
|---|---|---|---|
| End of second reaction | 17.6% | NM[1] | 79.8% |
| After extraction 1 | 13.9% | 10.7% | 67.2% |
| After extraction 2 | 14.6% | 11.4% | 69.6% |
| After extraction 3 | 14.2% | 10.6% | 69.3% |
| End of distillation | 12.75% | 0.94% | 78.3% |
| Isolated Compound 9 | LT DL | LT QL | 99.4% |

[1]Not identified due to different analytical method

Table 8 shows that during extractions the ability to purify the product of both impurities (TA and hexyl bromide) is poor. However, after distillation there is a significant reduction in the amount of hexyl bromide but not in TA. The limited ability of removing both impurities in extractions can be explained by their organic nature and poor water solubility (hexyl bromide is insoluble in water and TA has solubility of 0.5 mg/ml). TA and hexyl bromide have both high boiling point (188° C. and 154° C. respectively). The solubility of both impurities is high in toluene as well as in a mixture of toluene and heptane. The mixture of toluene and heptane leads to total removal of both impurities and high purity Compound 9-FB.

Removal of THF from Compound 9

The process of Example 1 may lead to a pridopidine-HCl product that is undesirable due to high levels of Compound 3 impurity as shown by Scheme 3. The formation of this impurity was studied and its precursor Compound 11 was identified in Compound 8 (step II). It was found that Compound 11 is an oxidation product of 1,4-bis((3-(1-propyl-1,2,3,6-tetrahydropyridin-4-yl)phenyl)thio)butane impurity found in Compound 10. This impurity was formed during acidic elimination of Compound 9 in the presence of traces of THF from step I. The level of THF in Compound 9-FB obtained from the present work-up was examined and is set forth in Table 9.

Scheme 3: Formation of Compound 3 in the pridopidine synthesis process

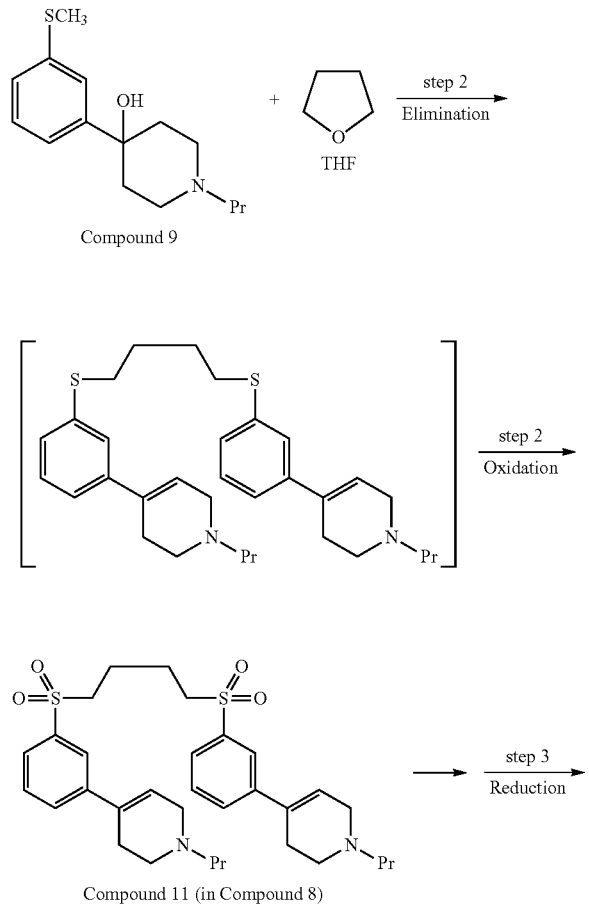

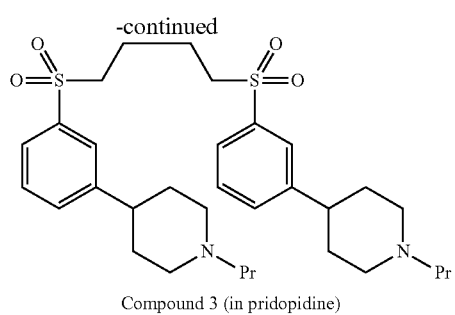

Compound 3 (in pridopidine)

TABLE 9

Level of THF in Compound 9-FB laboratory batches

| | Exp. No. | | | | | | |
|---|---|---|---|---|---|---|---|
| 1501 | 1401 | 1502 | 1403 | 1504 | 1505 | 1506 | 1507 |
| THF level | | | | | | | |
| 79 ppm | 23 ppm | 84 ppm | <RL | <RL | 21 ppm | 22 ppm | 7 ppm |

Table 9 shows that THF is efficiently removed by Compound 9-FB work-up.

The Compound 9-FB work-up described in this example addresses all of the problems raised in the work-up of Example 1. Water washings remove salts that formed during the process and the quenching, resulting in high assay close to the chemical purity levels. The evaporation provides good removal of THF and other organic impurities with minimal intermediate losses. The controlled crystallization provides shorter filtration time due to better solid characteristics. The drying stage provides good control over material assay that is important to the next stage's operability and also reduces the amount of THF to ppm levels.

Scale-Up Results of Compound 9 According to the Process Described in Examples 2 and 3.

Table 10 summarizes the quality results of all compound 9 scale-up batches according to the recommended specification. The impurity profile method is based on percent area.

TABLE 10

Purity profile of compound 9 scale-up batches

| Exp. No. | Assay | Cmpd 9 (CP) | Cmpd 12 | TA | 3BTA | Total Impurities |
|---|---|---|---|---|---|---|
| Recommended specifications | ≥95.0% | Report value | ≤0.8 | Report value | Report value | ≤3.5 |
| 1601 | 99.9% | 99.5% | 0.20% | <0.06% | <0.05% | 0.28% |
| 1602 | 99.3% | 99.3% | 0.23% | <0.06% | <0.05% | 0.50% |
| 1603 | 97.0% | 98.2% | 0.24% | <0.06% | <0.05% | 1.53% |
| 1604 | 97.4% | 98.6% | 0.20% | <0.06% | <0.05% | 1.15% |
| 1605 | 97.8% | 98.6% | 0.31% | <0.06% | 0.14% | 0.96% |
| 1606 | 99.9% | 98.3% | 0.19% | <0.1% | <0.04% | 2.11% |
| 1607 | 102.1% | 98.9% | 0.18% | <0.06% | <0.04% | 1.31% |
| 1608 | 99.9% | 98.3% | 0.15% | <0.1% | <0.04% | 1.73% |
| 1609 | 100.8% | 98.4% | 0.20% | <0.1% | <0.04% | 1.15% |
| 1610 | 101.7% | 99.4% | <0.04% | <0.1% | <0.04% | 0.61% |

Assay & CP

The recommended specification for assay is not less than 95.0%. All the batches have higher assay than the suggested limit. High assay shows that the workup efficiently removes organic and inorganic impurities. Effective filtration and drying techniques remove traces of n-heptane, toluene and TA. The batches of Compound 9 have similar CP and assay levels.

Compound 13 Impurity

The level of Compound 13 in batches manufactured according to the procedures set forth in Example 1 was 0.46-1.36%. When Compound 13 was >1.2%, the pridopidine-HCl was out of specification (OOS) due to high level of Compound 13.

Scheme 4: From Compound 12 in Compound 9 FB to Compound 13 in pridopidine-HCl

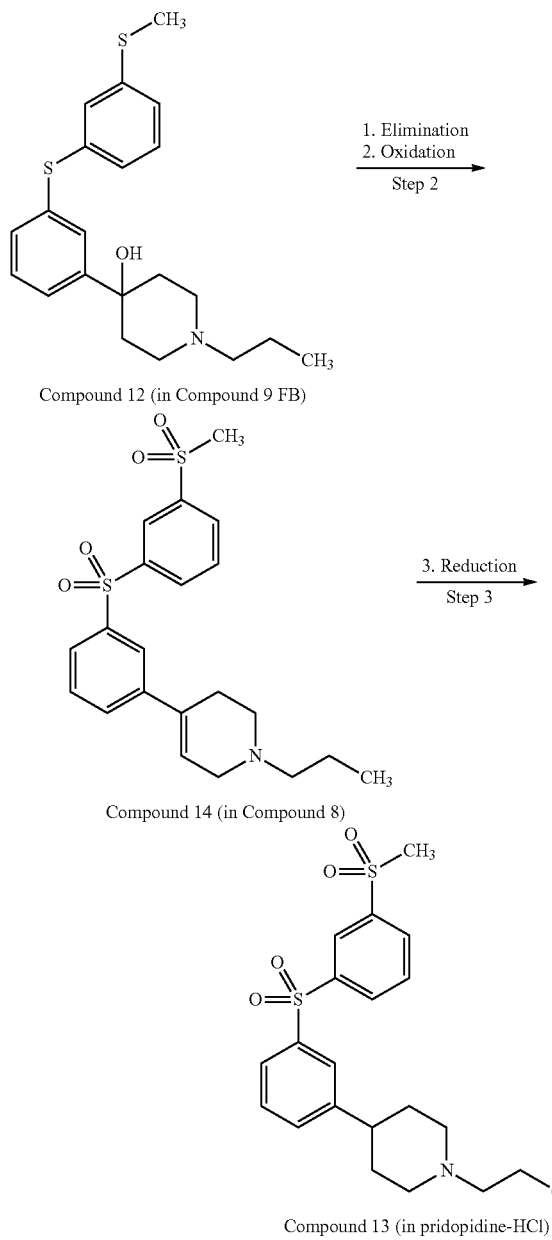

The level of the Compound 12 in scale-up batches was between 0.04%-0.30%, which is significantly lower than batches manufactured according to Example 1 and the specification limit. In this aspect, flow reaction has an advantage on cryogenic batch reaction since the time of the lithiation reaction is a few seconds compared to hours in the batch process. Even when the lithiation reaction is performed at a higher temperature, e.g. 2-8° C., the formation of Compound 12 is still slow.

TA and 3BTA

TA and 3BTA are liquids and are detected in both $IPC_2$ chromatography and the mother liquor (ML) after filtration of Compound 9. TA can be formed either when 3LTA reacts with water during the quenching or as a side reaction when it extracts hydrogen α to the 1P4P ketone. 3BTA can be in the quenched mixture when not all of it has reacted with HexLi.

TABLE 11

TA and 3BTA Area % in Production Stages

| Batch Number | Composition In Quenched Mixture (% Area) | Composition in Solid Compound 9 After Workup (% Area) |
| --- | --- | --- |
| 1601 | TA = 13.5% | TA = LT 0.05% |
|  | 3BTA = 0.7% | 3BTA = LT 0.06% |
| 1602 | TA = 15.0% | TA = LT 0.05% |
|  | 3BTA = 4.3% | 3BTA = LT 0.06% |
| 1603 | TA = 14.0% | TA = LT 0.05% |
|  | 3BTA = 4.3% | 3BTA = LT 0.06% |
| 1604 | TA = 26.9% | TA = LT 0.05% |
|  | 3BTA = 33.0% | 3BTA = LT 0.06% |
| 1605 | TA = 25.4% | TA = LT 0.05% |
|  | 3BTA = 43.1% | 3BTA = 0.14% |

Table 11 shows that large amounts of 3BTA and TA in the quenching mixture are easily purified in the workup of scheme 2, which gives Compound 9 with only traces of 3BTA and TA.

Level of THF Residual Solvent

Amount of THF in Compound 9 is very important since THF reacts in the $2^{nd}$ stage with Compound 9 to give 1,4-bis((3-(1-propyl-1,2,3,6-tetrahydropyridin-4-yl)phenyl)thio)butane followed by oxidation to Compound 11 and finally reduction in the 3' stage to give Compound 3. In the scale-up batches THF is removed so efficiently that Compound 9 has a negligible amount of THF (0-19 ppm). Table 12 provides levels of THF in various batches.

TABLE 12

THF Level in Compound 9

| Batch Number | THF level |
| --- | --- |
| 1601 | 19 ppm |
| 1602 | 3 ppm |
| 1603 | 3 ppm |
| 1604 | 0 ppm |
| 1605 | 0 ppm |
| 1606 | 0 ppm |
| 1607 | 0 ppm |
| 1608 | 0 ppm |
| 1609 | 0 ppm |
| 1610 | 13 ppm |

Table 12 shows clearly that all scale-up batches contain low levels of THF, if any.

Compound 16 in Compound 9

In batches of Compound 9 prepared using the procedure of Example 1 the level of Compound 16 was typically 0.05-0.09% area in the lab, and 0.11-0.14% in the production. However, the level of this impurity in the ML is between 3-17% due to the hydrophilic character of its di-salt.

Scheme 5: Compound 16 structure and formation mechanism

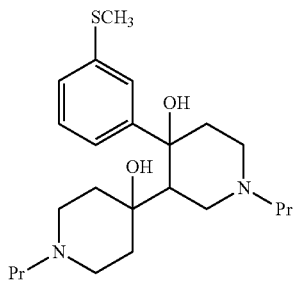

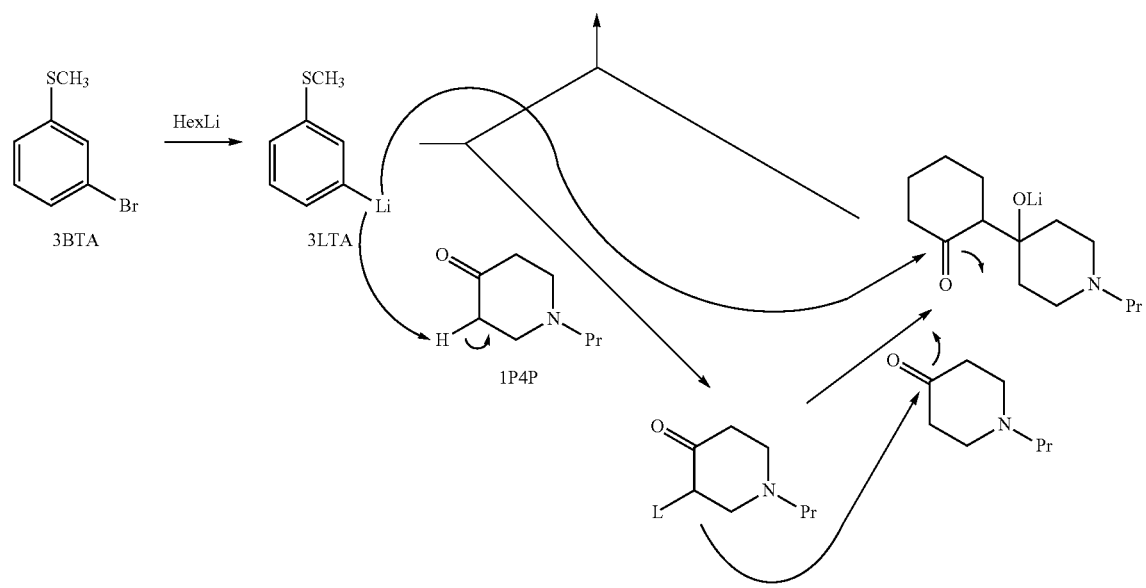

Low levels of Compound 16 (0.06-0.07%) were identified in only two out of ten Compound 9 scale-up batches. This impurity was not detected in the ML or the IPC samples. Without wishing to be bound to this theory, it is the short coupling reaction time that prevents Compound 16 formation.

Example 4: Development of Pridopidine Step 2 of Scheme 2: Compound 8 Free Base

Significant improvements over the second step of the procedure of Example 1 are described below. The assay and the yield of Compound 8-FB were dramatically improved due to the more controlled elimination reaction. The higher purity of Compound 9-FB enables a reduced elimination temperature. Moreover the number of extractions and the types of extractions were optimized.

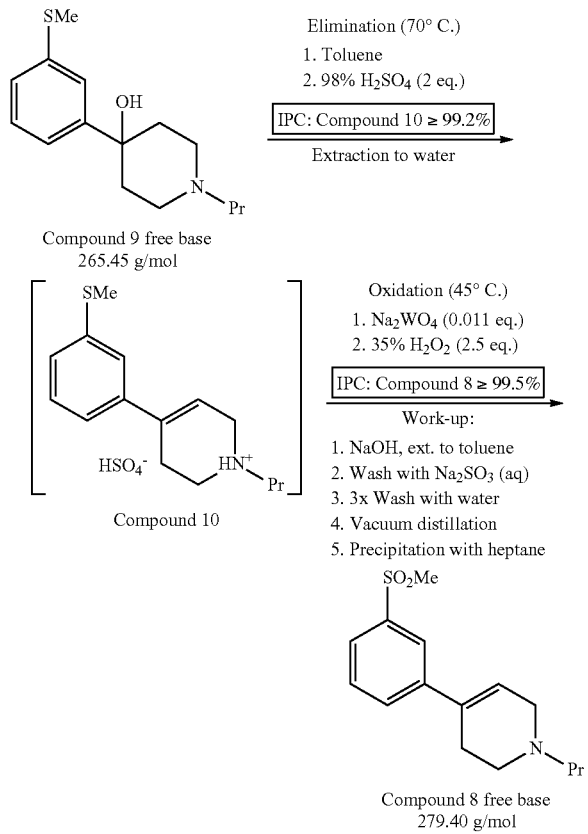

Example 4.1: Compound 8-FB Preparation

Compound 8 was prepared following the synthesis hereinbelow:

Solid Compound 9 FB is charged into reactor followed by 5 Vol of toluene. The mixture is warmed up and mixed at 45° C. (Tr=40-50° C.). 0.38 Vol of 95-98% sulfuric acid is added dropwise, keeping the temperature below 80° C. (1.9 eq, exothermic addition, Tr=30-90° C.). When the acid addition is finished, the mixture is warmed with good stirring to 70° C. for the elimination reaction (two phase system, Tr=60-80° C.). The two phases are mixed together with good mixing for not less than 3.0 h at 70° C. The conversion is analyzed by IPC from a sample taken from the sticky lower phase. The elimination reaction is run to completion when Compound 10≥99.9%. After the conversion has completed, the mixture is cooled down to 30° C. (Tr≤40° C., no stopping point). Five (5) Vol of water are added and mixed at least for 20 min at 30° C. for extraction (Tr=20-40° C.). The phases are separated and the upper toluene phase is removed after at least 30 min at 30° C. It is important to move directly to the next stage. 0.014 w/w of sodium tungstate dihydrate (0.011 eq) is added to the mixture at 25-35° C. The mixture is warmed to 40° C. and 1.0 w/w of 30%-35% hydrogen peroxide (2.5 eq) is slowly added, keeping the temperature at Tr=30-55° C. The two oxidation reactions are very exothermic and take place sequentially. It is thus critical to keep temperature at Tr≤58° C. in order to obtain a product with a high assay. First, 0.5 w/w 30%-35% hydrogen peroxide is added, and after 20 min, when the second exothermal has started and finished, the second half is added). After the addition of all the hydrogen peroxide and the end of the exothermal reaction, the mixture is warmed to 50° C. (Tr=45-55° C.) and mixed for at least 2 h to finish the reaction. The conversion is analyzed by IPC and run to completion when Compound 8≥99.50%. (Corrective action: wait for another hour and add more hydrogen peroxide if needed). The reaction mixture is cooled down to 30° C. and the catalyst is filtered and washed with 1 Vol of water (Tr=25-35° C.). Five (5) Vol of toluene are added. The reactor needs to be purged with nitrogen through a vent and 40% sodium hydroxide (aq.) added to adjust the pH in the water phase to above 11 (Tr≤25° C., ~1-1.5 Vol, pH~13, $O_2$<11%, under $N_2$ conditions). The mixture is mixed for at least 45 min at 30° C. (Tr≤40° C., oxygen is formed and needs to be bubbled up from the water phase). The mixing is stopped to allow the phases to separate, giving a cloudy green aqueous phase which is removed after 45 min (first extraction). Four (4) Vol of 5% sodium sulfite (aq.) are added and mixed for at least 30 min at 30° C. to quench the peroxide residue. The mixing is stopped to allow the phases to separate, giving a slight cloudy aqueous phase which is removed after 20 min (second extraction, should be measured with KI paper for peroxides, LT 20 ppm). Another three water washes are performed with 5 Vol of water at 30° C. for purifying the product (pH≤10). The reaction mixture is distilled under vacuum when the pressure is reduced to P≤80 mbar, the Tj is carefully warmed up from 15° C. to 65° C. until 2-3 Vol of toluene remain in the reactor (Tc=0-5° C., Tr=15-40° C., Tj≤70° C.). After vacuum distillation 4 Vol of n-heptane are added at 40° C. for at least 15 min and a heavy slurry is formed. The reaction mixture is cooled down to 0-10° C. and stirred for no less than 4 h. The solid is filtered and washed with 2 Vol cold n-heptane (<10° C.) to remove the crust from the reactor (more cold n-heptane washes could be added for removing the crust if any). The wet cake is dried under vacuum (P<50 mbar) at 40° C. to constant weight (approximately 4-8 h). Dried Compound 8 is obtained at a 70%-90% yield.

Example 4.2: Improving the Elimination Reaction

The process of Example 1 to make Compound 8 is a telescoped process containing 3 chemical reactions—elimination followed by two successive oxidations. Compound 8-FB is formed from Compound 9-FB through two non-isolated intermediates: Compound 10 and Compound 7. The first reaction is water elimination from Compound 9-FB to Compound 10-sulfate. Elimination starts with the addition of toluene and concentrated sulfuric acid to obtain Compound 9-HCl. The solution is then distilled to remove water which is the driving force for the elimination. The reaction takes a couple of hours since it proceeds by azeotropic distillation at high temperature (110-116° C.).

Temperature of the Elimination Reaction

Reproducing Compound 8 by the process of Example 1 gave very low yield and purity (Yield=19.9% total imp=1.86%).

In order to avoid the long time required to heat the elimination reaction, the temperature was lowered and the conversion of Compound 9-FB to Compound 10 (using 2 eq of sulfuric acid) was followed. Table 13 shows data from such a synthesis.

TABLE 13

Conversion of elimination reaction at different temperature:

| Exp. No. | Temp [° C.] | Conversion [% Compound 10] | Impurities in Compound 8 | CP [Compound 8] | Yield [%] |
| --- | --- | --- | --- | --- | --- |
| 1701 | 114° C. | 99.83% after 01:10 hr | Compound 7 <0.03% Compound 9 = 0.02% Total unknowns = 0.64% | 99.2% | 52% |
| 1702 | 57° C. | 99.18% after 06:00 hr 99.21% after 22:00 hr | Compound 7 = 0.07% Compound 9 <0.02% Total unknowns = 0.32% | 99.4% | 82% |
| 1703 | 70° C. | 99.16% after 02:00 hr (mixed overnight at r.t.) | Compound 7 = 0.04% Compound 9 <0.02% Total unknowns = 0.73% | 99.0% | 83% |
| 1704 | 80° C. | 99.21% after 01:30 hr (mixed overnight at r.t.) | Compound 7 <0.03% Compound 9 <0.02% Total unknowns = 0.92% | 98.9% | 87% |

Table 13 demonstrates the relation between the elimination reaction temperature and yield. Compared to the low yield of Compound 8 in Experiment No. 1701, the yield of Compound 8 was above 80% when the reaction was performed at a low temperature without azeotropic distillation (atmospheric azeotropic distillation). Unexpectedly the conversion was high even when water is not removed (conversion above 99.1%). The total impurities increased as reaction temperature increased from 57° C. to 70° C. and to 80° C. The reaction time was shorter when the temperature was between 57-80° C. Thus, it is likely that when the mixture was boiling, most of the reaction had completed after the temperature reached 110° C. for azeotropic distillation.

The recommended temperature for the elimination reaction to obtain a high yield and a low total impurities level is about 70° C.

Equivalent of Sulfuric Acid in the Elimination Reaction

In Example 1, 1 eq of 98% sulfuric acid was used together with 1 eq HCl and Compound 9-HCl salt. However, the present THF treatment allows the use of only 1.1 eq of sulfuric acid with Compound 9-FB. A relationship between high equivalent of sulfuric acid and low purity after the azeotropic distillation was identified.

Other Parameters of the Elimination Reaction

Reaction Time:

In experiment No. 1702 the conversion reached 99.18% after 6 hr at 57° C. Additional mixing overnight didn't change conversion (99.21% after 22 hr). This was similar to Experiment No. 1703, which after 2 hr at 70° C. gave 99.16% and after overnight stirring gave 99.10%.

Elimination Reaction Work-Up

The next telescopic reaction (two consecutive oxidizations) was completed in water as a solvent.

In the process of Example 1, when finishing the elimination, a series of extractions was completed. First water is added to the toluene-sulfuric acid to obtain 2 phases. Next, the pH is adjusted by 50% NaOH (aq) and the lower aqueous phase is discarded. Then water and sulfuric acid are added to the toluene phase until the pH is less than 2. After the extraction the toluene phase is discarded and the mixture is ready for oxidation reaction as a sulfate salt of Compound 10.

The work-up optimization in the present elimination process ends with Compound 10 sulfuric salt without the HCl salt. Moreover, the elimination reaction is purer compared to elimination reaction of Example 1. Therefore, only one extraction is required to extract the salt to the water phase and directly continue to the oxidation reaction. In

TABLE 14

Conversion to Compound 10 with different equivalent of sulfuric acid at 70° C.

| Exp. No. | 1 hr Conversion [% Compound 10] | 1.5 hr Conversion [% Compound 10] | Last conversion [% Compound 10] | CP [Compound 8] | Yield [%] |
|---|---|---|---|---|---|
| 1703 (2.0 eq) | 97.89% | 98.97% | 99.16% (2 hr) | 99.0% | 83% |
| 1901 (2.5 eq) | 96.86% | 97.89% | 98.51% (2 hr) | 98.9% | 83% |
| 1902 (1.1 eq) | 11.18% | 11.15% | [1]99.21% (2.5 hr) | 98.9% | 83% |
| 1903 (5.0 eq) | Not sampled | Not sampled | [2]100% (3 hr) | NM | 0% |
| 1904 (1.8 eq) | 93.11% | [3]96.92% | Not sampled | 99.5% | 87% |

[1]In this experiment, after 1.5 hr, 0.9 eq of sulfuric acid was added to complete the reaction.
[2]Full conversion but low purity that can be seen in the IPC chromatography. The Compound 8 could not be isolated.
[3]This experiment did not continue to a full conversion.

When using 2.0 eq of 98% sulfuric acid, the conversion of Compound 10 reached a sufficiently high level of conversion after 2 hr. Thus, higher equivalents of sulfuric acid should have been expected to increase conversion rate, however, this was not found when using 2.5 eq of 98% sulfuric acid where yield and purity was similar to 2.0 eq. Using 1.1 eq gave poor conversion after 1.5 hr but it was found that addition of 0.9 eq sulfuric acid (total of 2 eq) is an effective corrective action giving similar results as a reaction with 2 eq from the beginning Adding 5.0 eq of sulfuric acid completely deteriorate the reaction. With 1.8 eq the reaction is somewhat slower but gives similar results as 2 eq. Therefore it is recommended to use 2.0 eq of sulfuric acid at 70° C. for 3.5 hr to be sure that a steady maximal conversion has been achieved. Sulfuric acid is not only the dehydrating reagent, the reaction solvent is also a dehydrating reagent. Therefore, there should be enough equivalents to solubilize Compound 9-FB.

Experiment No. 1702 only one extraction was completed and there was no effect on yield and purity (yield=82%, total impurities=0.57%). This improvement simplifies the process and saving time, reagents and solvents.

Example 4.3: The Oxidation Reaction

The oxidation step is comprised of two consecutive oxidation reactions. The reaction time decreased (1.5 hr) due to an improvement in the purity of Compound 10 and the work-up was improved to deal with impurity Compound 1. Unneeded extractions were removed and other effective washes with waters were added.

The importance of Temperature During Oxidation Reaction

Table 15 shows data from experiments in which the temperature of the oxidation reaction was kept at 50° C.

TABLE 15

Different oxidation reaction temperature effect on the assay

| Exp. No. | Temperature during H$_2$O$_2$ addition | Temperature during oxidation reaction | Chromatographic purity [% Compound 8] | Assay |
|---|---|---|---|---|
| 2001 | 38-62° C. | 50° C. | 98.7% | 96.4% |
| 2002 | 39-58° C. | 50° C. | 99.9% | 99.9% |

Example 1 has an oxidation reaction temperature range of 50±5° C. The table shows the effect of temperature during the reaction on the purity and assay of Compound 8. The reaction temperature can be kept stable at 50° C., however, if the temperature exceed 58° C. during hydrogen peroxide addition, the assay drops and Compound 8 solid appearance becomes green-brown color (Experiment 2001). The two oxidation reactions are very exothermic. The first oxidation reaction starts once the oxidizing reagent is added and the exothermic nature of the reaction is observed immediately. The second oxidation is a catalytic reaction and thus the exothermic nature of the reaction is delayed until the hydrogen peroxide addition and accumulation of reagent can give rise to a strong exothermic reaction. The critical temperature should be Tr≤58° C.

Scale-Up Results of Compound 8 According to the Process of Example 3

Table 16 summarizes the quality results of all compound 8 scale-up batches according to recommended specification.

TABLE 16

Quality Results of Compound 8 Scale-up Batches

| Parameter | Recommended Specification | Batch No. 2101 | Batch No. 2102 | Batch No. 2103 |
|---|---|---|---|---|
| IPC$_3$ (Compound 10) | Report value | 99.51% (2.0 h) | 99.59% (2.5 h) | 99.62% (2.0 h) |
| IPC$_4$ (Compound 8) | NMT 99.5% | 99.51% (1.5 h) | 100% (1.5 h) | 99.64% (1.0 h) |
| Description | White to yellow solid | White | White | White |
| Assay | NLT 99.5% | 100% | 100.4% | 100.0% |
| Compound 1 | Report value | 0.15% | 0.10% | 0.15% |
| Compound 9 | Report value | <0.02% | <0.02% | <0.02% |
| Compound 7 | NMT 0.10% | <0.03% | <0.03% | <0.03% |
| Compound 11 | NMT 0.2% | ND | NR | <0.02% |
| Compound 14 | NMT 0.36% | ND | ND | 0.05% |
| Any other imp. | NMT 0.2% | 0.09% | 0.13% | 0.08% |
| Total imp. | NMT 0.9% | 0.24% | 0.23% | 0.23% |

IPC$_3$ monitored the conversion in the elimination reaction (Compound 8 converts to Compound 10). All batches reached conversion of more than 99.5%.

IPC$_4$ monitored the conversion in the second oxidation reaction when Compound 7 (mono-oxidized, a sulfoxide compound) is converted to Compound 8 (di-oxidized, a sulfone compound). Residue of Compound 7 in isolated Compound 8 inhibits the reduction in the next reaction step (pridopidine crude) by poisoning the catalyst. The table shows that the workup of Compound 8 effectively removes 0.5% Compound 7 (Batch No. 2101 had 0.41% Compound 7 and 99.51% Compound 8). Table 16 also shows that all three scale-up batches met the recommended specifications. The powders of all the three batches were white in color, better than the solid yellow color in the lab scale. The assay results were also better than the lab scale (97-99%). Compound 9 was detected, as expected, in all batches but at less than the quantification limit because it is oxidized to Compound 1.

Compound 14, the oxidized form of the Compound 12 impurity has a level of 0.15-0.30%.

Compound 11, a precursor of Compound 3 impurity in the DS, was also not detected as expected since THF, the reason for 1,4-bis((3-(1-propyl-1,2,3,6-tetrahydropyridin-4-yl)phenyl)thio)butane in Compound 9, was very low.

To summarize, the quality of Compound 8 in the scale-up batches were better than the quality of Compound 8 in the batches prepared by the process of Example 1.

Example 5: Development of Procedure for the Purification of Compound 1 in Compound 8 in Scheme 2

This example describes reducing Compound 1 levels in Compound 8 as shown in Scheme 2 and improving its assay. This procedure involves dissolving the Compound 8 in 5 Vol toluene at 20-30° C. and adding 5 Vol of water followed by 3×5 Vol water washes. The toluene mixture was then distilled up to 2.5 Vol in the reactor and 4 Vol of heptane are added for crystallization. Two experiments were run (Experiment Nos. 2202 and 2203), the first one with neat toluene and the second with 5% IPA in toluene. The purification of Compound 1 is made possible in this system because Compound 1 is more hydrophilic than Compound 8 (i.e., hydroxyl group compared to double bond) and thus more soluble in water or water/IPA. Table 17 summarizes the results.

TABLE 17

Compound 1 Level in Compound 8 Rework Procedure

| Related Substance | Exp. No. 2201 (Compound 8) | Exp. No. 2202 (Crude rework) | Exp. No. 2203 (with 5% IPA) |
|---|---|---|---|
| Compound 1 | 0.45% | 0.30% | 0.28% |
| Compound 7 | <DL | <DL | <DL |
| Compound 9 | 0.08% | <DL | <DL |
| Compound 11 | <DL | <DL | <DL |
| Compound 14 | <QL | <DL | <DL |
| Total unknown | 0.33% | 0.07% | 0.07% |
| Total imp. | 0.78% | 0.37% | 0.35% |
| Assay | 102.0% | 101.8% | 103.5% |
| Yield | 86% w/w | 92% w/w | 93% w/w |

Table 17 shows that this procedure effectively purifies Compound 1, reducing its level by factor of 1.6 in Compound 8, improves the assay, and gives a reasonable yield (>90%). Purification of Compound 1 using 5% IPA/toluene as the organic solvent is slightly better for reducing Compound 1 levels and the assay of Compound 8. Compound 14 is an impurity found in Compound 8.

Addition of Hydrogen Peroxide in Two Portions

Hydrogen peroxide is used for oxidation in the second reaction stage of Compound 8. The allowed temperature range of the hydrogen peroxide addition is <58° C. When the temperature rises above 58° C., an epoxide impurity can form and hydrolyze to the Compound 4 impurity and the assay may be reduced. During hydrogen peroxide addition (in one portion as described in Example 1 the temperature rose to 68° C. for 5 min in batch no. 2101, despite the fact that the addition was very slow and took more than 1 h. Thus the hydrogen peroxide addition mode was changed in order to solve the spontaneous temperature elevation by splitting into two portions of 1.25 eq each and waiting for the accumulated heat to be released between the two additions.

When plotted on a graph of time (minutes) vs $H_2O_2$ mass added (g)/$T_{reactor}$ (° C.)/$T_{jacket}$ (° C.)/qr_rtc (W), the first hydrogen peroxide addition curve shows that the heat evolved at the beginning of the addition and stayed constant up to oxidation completion, which occurs after the addition of 1 eq of hydrogen peroxide. The second heat evolution started after about 15 min, during which 0.25 eq participated in the second oxidation. This delay is a result of heat accumulation. A similar graph of the second oxidation which 1.25 eq was added, the curve shape indicates a different reaction behavior in which the heat accumulates and its release is delayed (catalytic reaction). This mode of addition is necessary in order to better control the reaction temperature and to prevent a runaway reaction that can occur if the entire oxidizing reagent had been added in one addition.

In the next two scale-up batches, the hydrogen peroxide addition was performed as follows: The first amount (1.25 eq) was added at a temperature between 35-55° C., while the reaction temperature was kept at 40° C., and the second hydrogen peroxide addition took place just after the second "mini exothermal" stage finished (part of the second oxidation ~20 min), then it was added at a temperature between 30-55° C. with the reaction temperature kept at 35° C. These two batches worked without any temperature deviation.

Example 6: Step 3 of Scheme 2: Pridopidine Crude

In Example 1, this step is a reduction reaction using formic acid as a hydrogen donor and palladium on carbon (Pd/C) as the catalyst. This reduction technique is performed at a low temperature, and with water as a solvent. The reduction technique is poorly exothermic. In the present example, water volumes are optimized and Pd/C was used to yield a more effective process with smaller amount of reagent. However, the most significant improvement was simplification of the work-up that originally included two solvent swaps requiring three distillations. The present work-up also provides better purification of Compound 1. The present work-up results in pridopidine crude, which is a free base with large crystal solid. This pridopidine crude is easier to produce with high yield and has the same purity as the procedure of Example 1.

Pridopidine Crude Free Base Preparation—Present Procedure

Pridopidine crude free base was prepared according to the following procedure: Solid Compound 8 FB is charged into the reactor followed by 2.5 Vol of water. The mixture is cooled to Tr=10° C. (Tr<15° C.). 0.7 Vol of FA is added dropwise, keeping the Tr<20° C. (slightly exothermic). The slurry dissolves and Compound 8 formate salt is formed. The mixture is kept at 10° C. (Tr=5-15° C.). The reactor is purged with nitrogen and 0.1% w/w of 10% Pd/C wet catalyst is charged, followed by another nitrogen wash (slightly exothermic addition, Tr<20° C., 0.08-0.12% w/w Pd/C No. 402). When the addition is finished, the black mixture is warmed with good stirring to 30° C. for the reduction reaction (heterogenic system, Tr=20-35° C.). The mixture is mixed for NLT 3.5 h at 30° C. until the reaction has finished (reaction time could be between 2-15 h due to its stability in these conditions). The conversion is analyzed by IPC when the sample is filtered from the catalyst. The reaction is run to completion when Compound 8≤0.50%. After the reaction is complete, the mixture is filtered to remove the catalyst and washed with 2 Vol of water at Tr=25-35° C. The filtrate is collected by another reactor with 5 Vol of toluene. The two phases are mixed together and cooled to Tr<15° C. Thereafter, 40% aqueous sodium hydroxide is slowly added to adjust the pH in the water phase to between pH 11-14 and the solution is mixed for at least 30 min at 30° C. (Tr≤40° C., ~0.8 Vol 40% NaOH, pH~13). The mixing is stopped to allow the phases to separate, providing a clear yellow aqueous phase which separated after 20 min. Another three washes are performed with 5 Vol of water at 30° C. to purify the product (pH<11). In the last phase separation the interphase, if present, should be removed. The reaction mixture is cooled down to 15° C. (Tr=10-20° C.) for vacuum distillation. The clear mixture is distilled under vacuum when the pressure is reduced to P≤80 mbar, the Tj is carefully warmed up to 30-45° C. until 2-3.0 Vol of toluene remained in the reactor (Tc=0-5° C., Tr=15-45° C., Tj≤65° C., foamy distillation as long as water still remains in the reaction mixture). After the vacuum distillation has completed, 4 Vol of n-heptane are added at 30-40° C. to form a slurry. The slurry is warmed to 45-55° C. and mixed for dissolution. The clear yellow solution is cooled down to 42° C. and mixed for 4 h for crystallization (if the solution is still clear after 1 h, seeding is required). The heavy slurry is cooled down to 0° C. for 4 h and is stirred for not less than 4 h. The solid is filtered and washed with 2 Vol n-heptane to remove the crust, if present, from the reactor. The wet cake is dried under vacuum (P<50 mbar) at 40° C. to constant weight (approximately 2-4 h).

Example 6.1: Pridopidine Crude Step

Amount of Catalyst in the Reduction

Example 1 uses 15% w/w Pd/C catalyst for the reduction. Previously, when attempting to reduce the amount of the catalyst, the reaction proceeded slower and full conversion did not occur until more than 22 hours. A more efficient catalyst is needed in order to reduce the amount of catalyst used for benefit of the environment and to minimize costs associated with the process.

Table 18 shows data resulting from performing the method with catalysts from different sources.

TABLE 18

Adjusting Pd/C catalyst to reduction, loading and temperature study.

| Exp. No. | Catalyst Type | % w/w Catalyst | Temp | Conversion |
|---|---|---|---|---|
| 2301 | Sigma 10% Pd/C | 7.5% | 50° C. | 2.3% after 1 hr<br>2.4% after 4 hr<br>4.3% overnight |

TABLE 18-continued

Adjusting Pd/C catalyst to reduction, loading and temperature study.

| Exp. No. | Catalyst Type | % w/w Catalyst | Temp | Conversion |
|---|---|---|---|---|
| 2302 | Sigma 10% Pd/C | 15% | 30° C. | 76.0% after 2 hr 99.9% after 3.5 hr |
| 2303 | Sigma 10% Pd/C | 15% | 40° C. | 99.9% after 2.5 hr |
| 2304 | JM type 425 5% Pd/C | 10% | 40° C. | 13.2% after 4.5 hr 30.3% overnight |
| 2305 | JM type 487 10% Pd/C | 5% | 40° C. | 8.8% after 1 hr 12.9% after 4 hr 38.8% overnight |
| 2306 | JM type 487 5% Pd/C | 10% | 40° C. | 21.3% after 4.5 hr 44.5% overnight |
| 2307 | JM type 402 10% Pd/C | 5% | 40° C. | 24.3% after 1 hr 39.1% after 4 hr 65.5% overnight |
| 2308 | JM type 402 10% Pd/C | 10% | 40° C. | 99.9% after 50 min |
| 2309 | JM type 402 10% Pd/C | 10% | 50° C. | 99.9% after 50 min |
| 2310 | JM type 402 10% Pd/C | 8% | 40° C. | 99.9% after 2.5 hr |

Table 18 above shows that catalyst loading affects the reaction rate more than a rise in temperature, however, temperature still accelerates the reaction. A reaction performed under the conditions of Example 1 was completed after 3.5 hr at 30° C. with 15% w/w catalyst. However, after changing catalyst to the more efficient Johnson Matthey (JM) type 402 catalyst (available from Johnson Matthey PLC), the reaction was completed after 2.5 hr at 40° C. with only 8% w/w catalyst (Experiment No. 2310). When the reaction temperature and catalyst type and amount are not optimized, the conversion may not reach its highest value. In this case, time will not be the corrective action.

It is recommended to use 8% w/w 10% Pd/C 50% wet JM type 402 catalyst at 30-40° C. for not less than 2.5 hr and analyze the conversion by IPC. If the conversion is lower than 99.5%, it is recommended to sample every 1hr to see the progress of the reaction. If two IPC results in a row are the same, more catalyst can be added.

Improve Pridopidine-FB Yield by Changing Reagent Addition Mode:

In Example 1 addition of FA is completed at 30-40° C. and the reaction time and isolated yields were not consist and not optimized. It was assumed that the FA addition is not optimal. Without wishing to be bound to theory, this can be explained by the fact that the reduction reaction needs both FA as hydrogen donor and Pd/C as catalyst simultaneously. The presence of the catalyst in the mixture when only part of the FA exists may create side reaction that can lower the yield. Thus, it was suggested to put the entire amount of FA together with the catalyst in cold temperature and warm it slowly to the reaction temperature. This addition technique is called "cold addition". Table 19 summarizes these experiments.

TABLE 19

Pridopidine Crude Cold Addition Experiments

| Exp number | Addition Mode | Reaction Condition | Reaction Rate (% pridopidine) | End of Reaction | Yield |
|---|---|---|---|---|---|
| 2311 | Base line experiment: Compound 8 was added at RT Water + 0.2 Vol FA was added at RT Pd/C was added at RT 0.5 Vol FA was added dropwise | 40° C. 10% Pd/C | 1 h 55.9% 2 h 86.2% 2.5 h 100% | 2.5 h Compound 8 is ND | 83% |
| 2312 | Cold addition: Compound 8 was added at RT Water was added at RT 0.7 Vol FA was added at 15° C. Pd/C was added at 9° C. Warm to 20° C. | 20° C. 10% Pd/C | 1 h 9.1% 2 h 21.8% 3 h 30.5% 4 h 44.6% 5 h 72.1% 6 h 97.1% | 6 h Compound 8 is 0.2% | 92% |
| 2313 | Cold addition: Compound 8 was added at RT Water was added at RT 0.7 Vol FA was added at 20° C. Pd/C was added at 10° C. Warm to 30° C. | 30° C. 10% Pd/C | 1 h 24.8% 2 h 65.3% 2.5 h 95.3% | 2.5 h Compound 8 is 0.8% | 91% |
| 2314 | Cold addition: Compound 8 was added at RT Water was added at RT 0.7 Vol FA was added at 21° C. Pd/C was added at 10° C. Warm to 30° C. | 30° C. 10% Pd/C | 1.1 h 35.7% 2 h 76.4% 2.5 h 98.9% stirring overnight 99.3% | 2.5 h Compound 8 is 0.10% | 90% |
| 2315 | Cold addition: Compound 8 was added at RT Water was added at RT 0.7 Vol FA was added at 19° C. Pd/C was added at 10° C. Warm to 25° C. | 25° C. 10% Pd/C | 3.5 h 30.3% 5.5 h 66.8% Stirring overnight 98.8% | Compound 8 is 0.14% | 88% |

Table 19 shows clearly that cold additions raise the yield by 6-9% compared to the base line experiment (Experiment No. 2311). According to Experiment No. 2313, it took 2.5 hours for the reaction to finish at 30° C. Experiment No. 2314 had identical reaction conditions as Experiment No. 2313 and had consistent kinetic and yield results. The reaction was expectedly slower at 25° C. and 20° C. compared to higher temperature. The reaction was also stable overnight. With a yield of 88-92% and mechanical loss of 7% (as described above), the mass balance can be close to 100%.

"Pridopidinium Impurity" (Compound 15), a Byproduct of the Reduction Step

The benefits of cold addition and reaction temperature on yield are now clear. Having a 7-9% yield improvement at low temperature compared to high temperature raised the question of what is the byproduct that is responsible for this yield loss. The reaction was performed in stress temperature conditions to investigate this question.

In Experiment No. 2316 all the reagents were put in RT according to the regular procedure and the reaction mixture was warmed to reflux. IPC (by HPLC) was taken to analyze the purity profile. The results are summarized in Table 20.

TABLE 20

Experiment No. 2316 Purity Profile (% area)
During Reduction in Reflux Condition

| Time | Tj (° C.) | Tr (° C.) | pridopidine C.P | Compound 8 | Compound 15 |
|---|---|---|---|---|---|
| 0 | 26 | 21 | 0.04% | 99.08% | 0.19% |
| 1 h | 110 | 79 | 75.31% | 17.77% | 6.08% |
| 2.5 h[1] | 110 | 75 | 78.68% | 14.27% | 6.24% |
| 5 h[2] | 110 | 72 | 81.64% | 11.12% | 6.35% |
| 6 h | 110 | 80 | 93.49% | <QL | 5.63% |
| Organic phase | 31 | 30 | 98.55% | 0.16% | 0.18% |
| Aqueous phase | 31 | 30 | 2.18% | ND | 96.74% |
| Before dis. | 30 | 30 | 98.88% | 0.15% | 0.03% |
| Dry crude | | | C.P = 99.2%, Assay = 99.1%, Y = 85% | <QL | ND |

[1]After 2.5 h the reaction rate was slow, 0.25 Vol FA was added.
[2]After 5 h 0.25 Vol FA and 3% Pd/C were added for finish the reaction.

Table 20 shows that during this reduction reaction, under reflux conditions, Compound 15 was formed and increased to ~5-6% area during the reaction. Compound 15 is completely extracted into the aqueous phase during the water washes and was not detected in the isolated dry product. The isolated yield (85%) shows that the reaction is stable in high temperature, Compound 15 can be found only in the water phase after basification. Without wishing to be bound to theory, its formation can be explained as follows: When the FA/Pd/C mixture cannot supply enough hydride to keep the reduction in pace, Pd/C can deprotonate the tetrahydropyridine derivative (Compound 8) to give the aromatic pyridinium derivate (Compound 15). This can occur if the reaction starts with all the Pd/C but only 28% of the FA (as in the original process) or when part of the FA escapes from the reactor in boiling conditions (as in Experiment No. 2316). In the present cold addition procedure, Pd/C is with the FA from the beginning and is thus forming hydride with FA (that reduced the double bond of Compound 8) and not available as a catalyst for the aromatization of Compound 8 to form the pyridinium derivate.

To summarize, the crude pridopidine process using the "cold addition" mode can consistently deliver high yields of between 80-95%. The yield is influenced by side reactions that relate to the reaction temperature and the availability of FA. The main side reaction is aromatization of Compound 8 to the pridopidinium Compound 15. There is no quality concern regarding Compound 15 since it is removed by the water washes.

Example 6.2: Pridopidine Crude—Work-Up Development

After the reduction, pridopidine HCl is precipitated by adding HCl/IPA to the solution of pridopidine free base in IPA in the process of Example 1. Prior to that, a solvent swap from toluene to IPA is completed by 3 consecutive vacuum distillations. The amount of toluene in the IPA solution affects the yield and it was set to be not more than 3% (IPC by GC method). The spontaneous precipitation produces fine crystals with wide PSD. In order to narrow the PSD, Example 1 accomplishes HCl/IPA addition in two cycles with cooling/warming profile.

The updated process is advantageous for crystallizing pridopidine free base over the procedure in Example 1 for two reasons.

First, it simplifies the work-up of the crude because the swap from toluene to IPA is not required. The pridopidine free base is crystallized from toluene/n-heptanes system. Only one vacuum distillation of toluene is needed (compared to three in the work-up of Example 1) to remove water and to increase yield.

Second, in order to control pridopidine-HCl physical properties. Pridopidine free base is a much better starting material for the final crystallization step compared to the pridopidine HCl salt because it is easily dissolved in IPA which enables a mild absolute (0.2μ) filtration required in the final step of API manufacturing.

Crystallization of Pridopidine Free Base in Toluene/n-Heptane System

First, crystallization of pridopidine free base in toluene/n-heptane mixture was tested in order to find the right ratio to maximize the yield. In order to obtain pridopidine free base, pridopidine-HCl in water/toluene system was basified with NaOH(aq) to pH≥12. Two more water washes of the toluene phase brought the pH of the aqueous phase to ≤10. Addition of n-heptane into the toluene solution resulted in pridopidine free base precipitation. Table 21 shows data from the toluene/n-heptane crystallization experiments.

TABLE 21

Toluene/n-Heptane crystallization system

| Exp. No. | Toluene/n-heptane system | Filtration temp and time | Yield | Mother liquor lost | Remainders in the reactor | Mass balance |
|---|---|---|---|---|---|---|
| 2401 | 3 Vol/4 Vol | 10° C. overnight | 77% | 12.0% | 5.6% | 95% |
| 2402 | 2 Vol/6 Vol | 10° C. 2 hr | 84% | 13.5% | 2.1% | 100% |

TABLE 21-continued

Toluene/n-Heptane crystallization system

| Exp. No. | Toluene/n-heptane system | Filtration temp and time | Yield | Mother liquor lost | Remainders in the reactor | Mass balance |
|---|---|---|---|---|---|---|
| 2403 | 3 Vol/6 Vol[1] | 10° C. overnight | 80% | 15.5% | 4.5% | 100% |
| 2404 | 3 Vol/9 Vol | 10° C. overnight | 80% | 12.0% | 5.5% | 98% |
| 2405 | 3 Vol/6 Vol | 10° C. overnight | 88% | 6.9% | 3.1% | 98% |
| 2406 | 2 Vol/4 Vol | 0° C. overnight | 89% | 5.3% | 2.3% | 97% |

[1]Add 10% NaCl (aq) washes

Table 21 shows that no pridopidine free base was lost during the extractions because the mass balances are closed to completion (>95%, the 0-5% mass deviation can refer to mechanical loss). However, the yield is affected from toluene/n-heptane ratio and total volumes, cooling temperature and mixing time at low temperature. The factor that most significantly affects the yield is the toluene/n-heptane ratio. The best yield is obtained from the 1:2 ratio presented in Experiment No. 2405 and Experiment No. 2406, in two different total volumes. When more heptane had been used in 1:3 ratio, a lower yield was obtained because the total volumes is higher (Experiment No. 2402). In addition, higher amounts of heptane cause precipitation on the reactor walls and makes the slurry viscous.

Effect of pH During Addition of Aqueous NaOH

The aqueous NaOH solution is used to neutralize the formic acid and to create a toluene soluble pridopidine free base out of the acid salt (pridopidine-formate). During the exothermic addition of aqueous NaOH solution pridopidine starts to precipitate in pH=7-8 but immediately dissolves in the toluene phase.

In Experiment No. 2301, neutralization was performed until the pH was 9 and the yield dropped dramatically to 12.4%, and 58.4% of pridopidine was found in all the collected water washes. Therefore, NaOH should be added to obtain a pH of greater than 10. If more NaOH is added and the pH exceed 14, more water washes will be required to lower the pH back to pH=9-10, which is the most effective pH to precipitate pridopidine base. Too many washes can also negatively influence the yield and produce more waste.

Compound 1 Levels in Pridopidine Crude

There is a need to design a work-up that purifies the impurity Compound 1.

TABLE 22

Level of impurity Compound 1 in the crude stage (Experiment 2407)

| stage | pridopidine [% area] | Compound 8 [% area] | Compound 1 [% area] | Compound 4 [% area] |
|---|---|---|---|---|
| After catalyst filtration and addition of NaOH (pH = 13) | 96.29% | 0.04% | 1.3% | 0.16% |
| Extraction I (aqueous phase, pH = 13) | 98.66% (<DL) | <DL (<DL) | 0.89% (23.0%) | 0.16% (<DL) |
| Extraction II (aqueous phase, pH = 11) | 99.28% (19.71%) | <DL (<DL) | 0.51% (16.8%) | 0.16% (<DL) |
| Extraction III (aqueous phase, pH = 9) | 99.77% (71.54%) | <DL (<DL) | 0.22% (7.44%) | 0.16% (<DL) |
| Final product | 99.68% | <DL | 0.18% | 0.15% |
| Mother liquor | 100% | <DL | <DL | <DL |

Table 22 shows the impurities levels through all the crude stages.

Water washes of the toluene phase efficiently extract Compound 1 as demonstrated by the level of Compound 1 before (1.3%) and after (0.22%) the washes. Therefore, 3 washes are added to the toluene phase in order to reduce the level of Compound 1.

Adding Distillation to Pridopidine Crude During the Work-Up

After this work-up procedure and the reduction reaction, the toluene volumes must be suitable to the extractions (5 Vol) and the precipitation procedure (2-2.5 Vol). Therefore reduction of the toluene phase volume is needed.

TABLE 23

Effect of the distillation addition on the yield

| Experiment No. | procedure | Yield |
|---|---|---|
| 2302 | Without distillation | 77% |
| 2303 | Vacuum distillation to 2.5Vol | 90% |
| 2310 | Vacuum distillation to 2.5Vol | 88% |
| 2408 | Vacuum distillation to 2.5Vol | 91% |

Table 23 shows that the yield was much improved after a vacuum distillation step was added. The toluene distillation not only reduced the total volume but also removed water and as a result the yield increased. The distillation was performed at the following conditions: Tj<70° C., P<80 mbar and Tc=0° C. The distillation should be started from low temperature (Tr=10-20° C.) and the jacket temperature should be slowly increased. Under these conditions the Tr during the distillation will be between 15-45° C. The final volume of toluene in the reactor after distillation should be 2-2.5, then 4 volumes of heptane may be added and a cooling profile may be employed in order to get maximal yield and large crystals.

Example 7: Development of the Procedure for the Purification of Compound 1 in Pridopidine Free Base The present example describes lowering Compound 1 levels in pridopidine free base. This procedure involves dissolving pridopidine FB in 5 Vol of toluene at 20-30° C., 5 Vol of water are added and after the mixing phases are separated and the organic phase is washed three times with 5 Vol water. The toluene mixture is then distilled up to 2.5 Vol in the reactor and 4 Vol of heptane are added for crystallization. Experiment No. 2501 was completed using this procedure. Table 24 summarizes the results.

TABLE 24

Compound 1 Level in pridopidine Crude Rework Procedure

| Related substance | Experiment No. 2502 (Crude) | Experiment No. 2501 (Crude rework) |
|---|---|---|
| Compound 1 | 0.29% | 0.17% |
| Compound 4 | 0.22% | 0.16% |
| Compound 8 | <DL | <DL |
| Unknown each | 0.05% | 0.05% |
| Total imp. | 0.51% | 0.33% |
| Assay | 98.9% | 99.2% |
| Yield | 94% w/w | 94% w/w |

Table 24 shows that this procedure effectively purifies Compound 1 (factor of 1.7) and Compound 4 (factor of 1.4).

Example 8: Step 4 in Scheme 2: Pridopidine Hydrochloride Process

This example discusses the step used to formulate pridopidine-HCl from pridopidine crude. The corresponding stage in Example 1 was part of the last (third) stage in which pridopidine-HCl was obtained directly from Compound 8 without isolation of pridopidine crude. In order to better control pridopidine-HCl physical properties, it is preferable to start with well-defined pridopidine free base which enables control on the exact amount of HCl and IPA.

Pridopidine-HCl Preparation—Present Procedure

Pridopidine-HCl was prepared according to the following procedure: Solid pridopidine crude was charged into the first reactor followed by 8 Vol of IPA (not more than (NMT) 0.8% water by KF) and the mixture is heated to Tr=40-45° C. (dissolution at Tr=25-28° C.). The mixture was then filtered through a 0.2 µm filter and transferred into the second (crystallizing) reactor. The first hot reactor was washed with 3.8 Vol of IPA. The wash was transferred through the filter to the second reactor. The temperature was raised to 65-67° C. and 1.1 eq of IPA/HCl are added to the mixture (1.1 eq of HCl, from IPA/HCl 5N solution, 0.78 v/w). The addition of IPA/HCl into the free base is exothermic; therefore, it was performed slowly, and the temperature maintained at Tr=60-67° C. After the addition, the mixture was stirred for 15 min and pH is measured (pH≤4). If pH adjustment is needed, 0.2 eq of HCl (from IPA/HCl 5 N solution) is optional. At the end of the addition, the mixture was stirred for 1 hour at Tr=66° C. to start sedimentation. If sedimentation does not start, seeding with 0.07% pridopidine hydrochloride crystals is optional at this temperature. Breeding of the crystals was performed by stirring for 2.5 h at Tr=64-67° C. The addition HCl line was washed with 0.4 Vol of IPA to give ~13 Vol solution. The mixture was cooled to Tr=0° C. The solid is filtered and washed with cooled 4.6 Vol IPA at LT 5° C. Drying as performed under vacuum (P<) at 30-60° C. to constant weight: Dried pridopidine-HCl was obtained as a white solid.

Purification of Compound 4 During Pridopidine-HCl Process

A relationship between high temperature in the reduction reaction and high levels of Compound 4 impurity have been observed. A reduction in 50° C. leads to 0.25% of Compound 4. For that reason the process of Example 1 limits the reduction reaction temperature to 30±5° C. since this is the final step and Compound 4 level should be not more than 0.15%. The present process has another crystallization stage by which Compound 4 can be purified.

TABLE 25

Level of Compound 4 impurity in pridopidine crude and pridopidine-HCl stages

| Crude Experiment No. | Level of Compound 4 In the crude | Followed cryst Experiment No. | Level of Compound 4 In the cryst |
|---|---|---|---|
| 2601 | 0.20% | OM-373 | 0.07% |
| 2310 | 0.11% | OB-1337 | 0.05% |
| 2408 | 0.12% | OB-1338 | 0.05% |

Table 25 shows that the pridopidine-HCl procedure yielded Compound 4 by factor of about 3. This means that the reduction reaction in the crude stage can be performed at a high temperature to provide a level of not less than 0.2%, which is an acceptable level.

Example 9: Removal of THF in Compound 9 to Control Compound 11 and Subsequent Compound 3 in Process to Make Pridopidine In the process of Example 1, an impurity, specifically Compound 3, was found to originate from THF present in step 2 (formation of Compound 8) of the pridopidine process. Example 9 provides a process which removes the THF in step 1.

The modified method for step 1 provides a product with an equal or improved impurity profile and less than 0.20% of the Compound 11 impurity in Compound 8. Also, the formed Compound 3 impurity in the final step, originating from Compound 11, should be well below 0.15% using intermediate Compound 8 from the modified process.

The process of this Example for producing pridopidine is detailed below in Scheme 7:

Scheme 7:

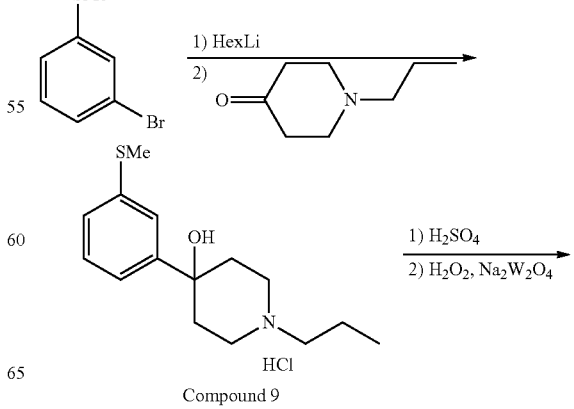

Compound 9

-continued

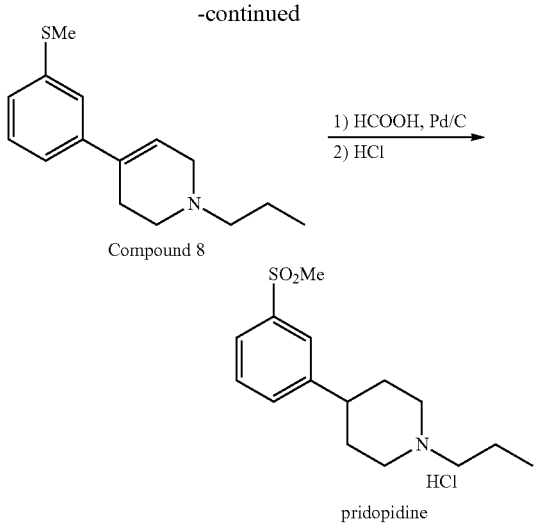

Compound 8

→ 1) HCOOH, Pd/C
2) HCl pridopidine

Method of Example 1

Step 1

HCl salt of Compound 9

Charge 3-bromothioanisole and THF at room temperature. Stir and cool the solution to below −70° C. Add 33% hexyl lithium in hexanes at below −70° C. over at least 60 minutes, and stir at this temperature until approved IPC. Add 1-propyl-4-piperidone at between −75 to −35° C. over at least 60 minutes and then stir the mixture at between −60 to −30° C. until approved IPC. The reaction mixture is quenched into a pre-cooled mixture of diluted HCl and MTBE while keeping the temperature under 0° C. Stir the mixture at 0±10° C. for at least 30 minutes. Filter the reaction mixture and wash the crystals with MTBE.

Removal and Control of THF by Vacuum Distillation of Acidic Water/Product Phase

The goal is to remove as much THF as possible from the Compound 9 product by vacuum distillation of the acidic water/Compound 9 phase that results after quenching of the reaction mixture.

Three experiments were performed here, Batches 2601, 2602 and 2603. All three experiments were performed in 3-L scale. The set-up was to follow the original method (Example 1) and lithiated 3-bromothioanisole followed by addition of piperidone and then quench the reaction mixture in water/HCl/MTBE mixture. The product, Compound 9, would be dissolved in water by slightly heating the two phase mixture and the major part of THF was removed by simply separating the aqueous phase from the organic phase. This provides a further advantage as many of the organic, non-amine containing impurities are effectively removed with the MTBE phase. For example, hexane, hexylbromide and thioanisole are all removed to a large extent prior to crystallization using this approach. The experiments are summarized in Table 26, hereinbelow.

TABLE 26

Experiments for removal of THF by vacuum distillation

| Batch | Experimental set-up |
|---|---|
| 2601 | 3-bromothioanisole was treated with hexyllithium 33% in THF at below −70° C. When reaction was complete, 1-propyl-4-piperidone was dosed in while keeping temperature below −35° C. After IPC showed a conversion of more than 83% (area) of Compound 9 the mixture was quenched with a pre-cooled water/HCl/MTBE mixture. The resulting slurry was then warmed to 50° C. Additional water was added and the mixture heated to 57° C. until all solids were in solution. The upper organic phase was discarded and the aqueous phase was left at 45° C. for 22 hrs and then at ambient temperature for an additional 4 days. The aqueous phase was next heated again THF was distilled off by vacuum distillation. Some bumping and frothing occurred during distillation. When ~250 mL of THF/water had been distilled off, the mixture was cooled down and treated with sodium hydroxide to free base Compound 9 which was subsequently extracted into MTBE and crystallized by slow addition of cHCl. |

TABLE 26-continued

Experiments for removal of THF by vacuum distillation

| Batch | Experimental set-up |
|---|---|
| | Result<br>THF level prior to distillation: 0.5% w/w<br>THF level after distillation: Not detected.<br>Purity by HPLC: 98.5%<br>Without wishing to be bound to theory, this very low level of THF already present before<br>distillation was caused by the long stationary time after quenching. However, it shows that<br>THF can effectively be removed by distillation from the acidic water phase. Filtration of the<br>product was not very fast and judged to be similar to what has been seen before in this scale,<br>i.e. not much better than what is seen in pilot plant. |
| 2602 | Experimental set-up<br>This experiment was run using the same procedures as Batch 2601 up to quench and<br>subsequent removal of MTBE.<br>The resulting slurry after quenching was warmed to 57° C. to get all solids in solution. Similar<br>to Batch 2601 additional water was needed. The upper organic phase was discarded. The<br>aqueous phase was re-charged into the reactor and THF was distilled off by vacuum<br>distillation. Some bumping and frothing occurred during distillation. When ~120 mL of<br>THF/water had been collected, the slurry was cooled down to 5° C. and the product was<br>isolated by filtration. Crystals were washed with water.<br>Result<br>THF level prior to distillation: 8.9% w/w<br>THF level after distillation: 0.5% w/w<br>THF level in isolated Compound 9: 195 ppm<br>Purity by HPLC: 99.6%<br>Level of Compound 11 in Compound 8 produced using this material: Below reporting limit.<br>Filtration and washing with water was deemed to be good. This is also reflected in the very<br>low level of THF in the final material. Purity was superior to when crystallized from MTBE<br>phase, primarily because early eluting impurities are removed very efficiently by<br>crystallization from water. |
| 2603 | Experimental set-up<br>This experiment was a repetition of Batch 2602 to verify the method, with regards to HPLC<br>purity and yield. Addition of 1-propyl-4-piperidone was performed using a straighter<br>temperature profile, i.e. it was performed without using an initial rapid temperature increase<br>in order to avoid formation of the late eluting impurity that was identified in Batch 2602 as<br>alkylated thioanisole. Alkylated thioanisole is formed by a reaction between lithiated<br>thioanisole and hexylbromide.<br>Result<br>THF level after distillation: 0.9%<br>Purity by HPLC: 99.8%<br>Level of Compound 11 in Compound 8 produced using this material: Below reporting limit<br>The method performed similarly in both Batch 2603 and Batch 2602. Yield was slightly<br>higher in Batch 2603. |

Results and Discussion:

THF Level and Formation of Compound 3

Vacuum distillation gives very good control of THF content both during the work-up as well as in isolated Compound 9. A low level of THF in the isolated Compound 9 material also ensures that the impurity Compound 3 is under control in the final API which was shown when material with low amount of THF was taken through to final product.

The exact level of THF that can be present prior to crystallization and isolation is difficult to determine because there is a strong likelihood that factors are scale-up dependent. A level of not more than 1.0% of THF in the aqueous phase prior to crystallization should be both practical to reach and low enough to ensure that the impurities Compound 11 and Compound 3 are under control. In the lab experiments, a level of between 0.5 and 0.9% THF in the aqueous phase resulted in a very low level of Compound 11 in Compound 8 and subsequent low level of Compound 3 in pridopidine.

Example Yield and Purity

The purity profile of the isolated Compound 9 was better when performing the crystallization from water (Batch 2602 and Batch 2603; both had purities over 99.5%) compared to both crystallization from water/MTBE mixture (purity of 98.5%) and pure MTBE (Batch 2601; purity was 98.5%). The major improvement is removal of early eluting/polar impurities. The yield of the present method may be slightly lower because there will be a small loss of material in the mother liquor. Estimated solubility of Compound 9 in the mother liquor at 5-20° C. is 0.8-0.9% (Batch 2602 and Batch 2603). In the current method this would correspond to 4-5% of the material being lost. This is considered an acceptable loss because of the improved purity of Compound 9.

Method for Large Scale

Charge 3-bromothioanisole and THF at room temperature. Carefully inert the system and keep the system inerted until quenched. Stir and cool the solution to below −70° C. Add 33% hexyl lithium in hexanes at below −70° C. (maximum −60° C.) over at least 60 minutes, and stir at this temperature for at least 30 min. and then until IPC shows conversion of not less than 99.5%. Add 1-propyl-4-piperidone at −75 to −35° C. over at least 60 minutes (care should be taken to avoid a rapid temperature increase at the start of addition as it has been shown that this may cause alkylation of the lithiated species by hexylbromide, see Batch 2602 and Batch 2603) and then stir the mixture at −60 to −30° C. for at least 30 minutes and then until IPC shows conversion of not less than 83.0%. Quench the reaction mixture into a pre-mixed and pre-cooled (0-10° C.) mix of water, HCl and MTBE while keeping the temperature below 20° C. The product will crystallize here. Heat the mixture to 55±5° C. and agitate vigorously for 15 min. The mixture separates into two clear layers without solids. If clear solutions/layers cannot be achieved, additional water may be charged. Let the layers separate and transfer the lower aqueous layer to another reactor. Filter the reaction mixture and wash the crystals with water. The mother liqueur may be circulated. The c-dry material is used as is in next step.

Conclusion

THF is controllable in step 1 by vacuum distillation from the aqueous product containing phase after quench. This allows for an easy and robust method of controlling also the formation of Compound 11 and the corresponding impurity Compound 3 in the final API.

Example 10: Chancing Mode of Addition of 3BTA and HexLi in Example 1

The reaction below (as described in Example 1) provides Compound 9 but also the side product Compound 12, Scheme 8

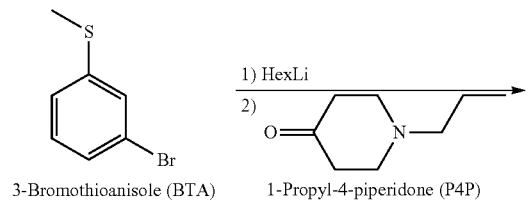

3-Bromothioanisole (BTA)    1-Propyl-4-piperidone (P4P)

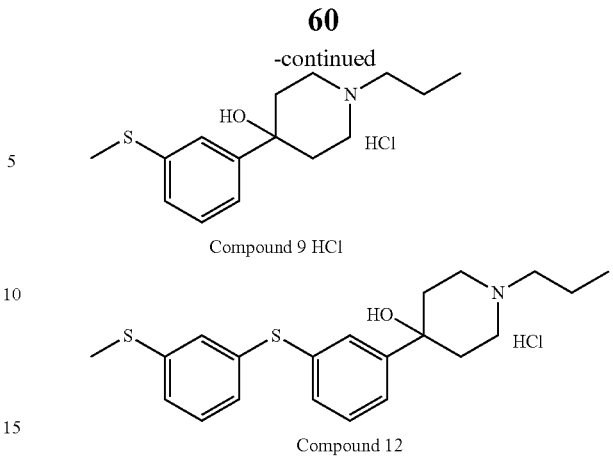

Compound 9 HCl

Compound 12

Table 27 provides examples of Compound 12 levels in Compound 9-HCl.

TABLE 27

Levels of Compound 12 in Compound 9-HCl in production

| Batch | Compound 12 (area-%) Limit ≤1.20 |
| --- | --- |
| 2701 (25 kg) | 0.53 |
| 2702 (100 kg) | 0.60 |
| 2703 (100 kg) | 0.55-0.62 |
| 2704 (100 kg) | 0.91-1.20 |
| 2705 (40 kg) | 0.46-0.84 |

Table 27 shows high levels of Compound 12 in experiments.

It was found that there is correlation between lithiation time and levels of Compound 12, specifically, the longer the lithiation time, the higher the content of Compound 12 in Compound 9.

A laboratory study was performed in order to understand the reason for high level of Compound 12 in Compound 9-HCl.

TABLE 28

| Normal addition (3BTA to HexLi/THF) | | | | |
| --- | --- | --- | --- | --- |
| Experiment No. | HexLi eq. | Temp (° C.) | HexLi addition time (h) | Hold time (h) | Compound 12 (area-%) |
| 2801 | 1.08 | −73 to −71 | 1.3 | 1 | 0.44 |
| 2802 | 1.05 | −75 to −71 | 3 | 20 | 0.49 |
| 2803 | 1.07 | −40 | 1 | 0.5 | 1.95 |
| 2804 | 0.86 | −78 to −73 | 12 | 11 | 1.50 |
| 2805 | 1.01 | −80 to −74 | 18.5 | 0.5 | 1.07 |
| 2806 | 1.07 | −72 to −71 | 8 | 1 | 0.92 |
| 2807 | 1.07 | −79 to −62 | 5 portions in 1 h | 1 | 0.34 |
| 2808 | 1.07 | −76 to −58 | 3 portions in 1 h | 1 | 0.28 |

Table 28 shows that in the standard process (3BTA addition to HexLi/THF), high levels of Compound 12 in Compound 9-HCl were found in different conditions. High levels were found when the temperature was high (Experiment No. 2803), when HexLi was in shortage (Experiment No. 2804) and when long HexLi addition time was employed.

These results led to suggest that the mechanism that leads to the formation of Compound 12 is the $S_NAr$ mechanism.

Reaction Mechanism

Since the simple changes described above, i.e. extractive washes or recrystallization of the free base, were not an option to solve the issue, another option to examine the previously unknown reaction mechanism and suppress Compound 12 in the synthesis was assessed.

BTA reacts with hexyllithium to give (I). The lithiated species then undergoes aromatic nucleophilic substitution with the second molecule of BTA to form compound (II), also called the Meisenheimer intermediate. The demethylation by nucleophile attack on compound (III) could either be from the bromide or amine moiety of 1-propyl-4-piperidone and results in compound (IV). The last transformation to give Compound 12 is the addition of lithiated species compound (IV) with 1-propyl-4-piperidone. In the literature, one paper was found (Ebenezer 2014) that supports the proposed mechanism.

Scheme 9: $S_NAr$ mechanism

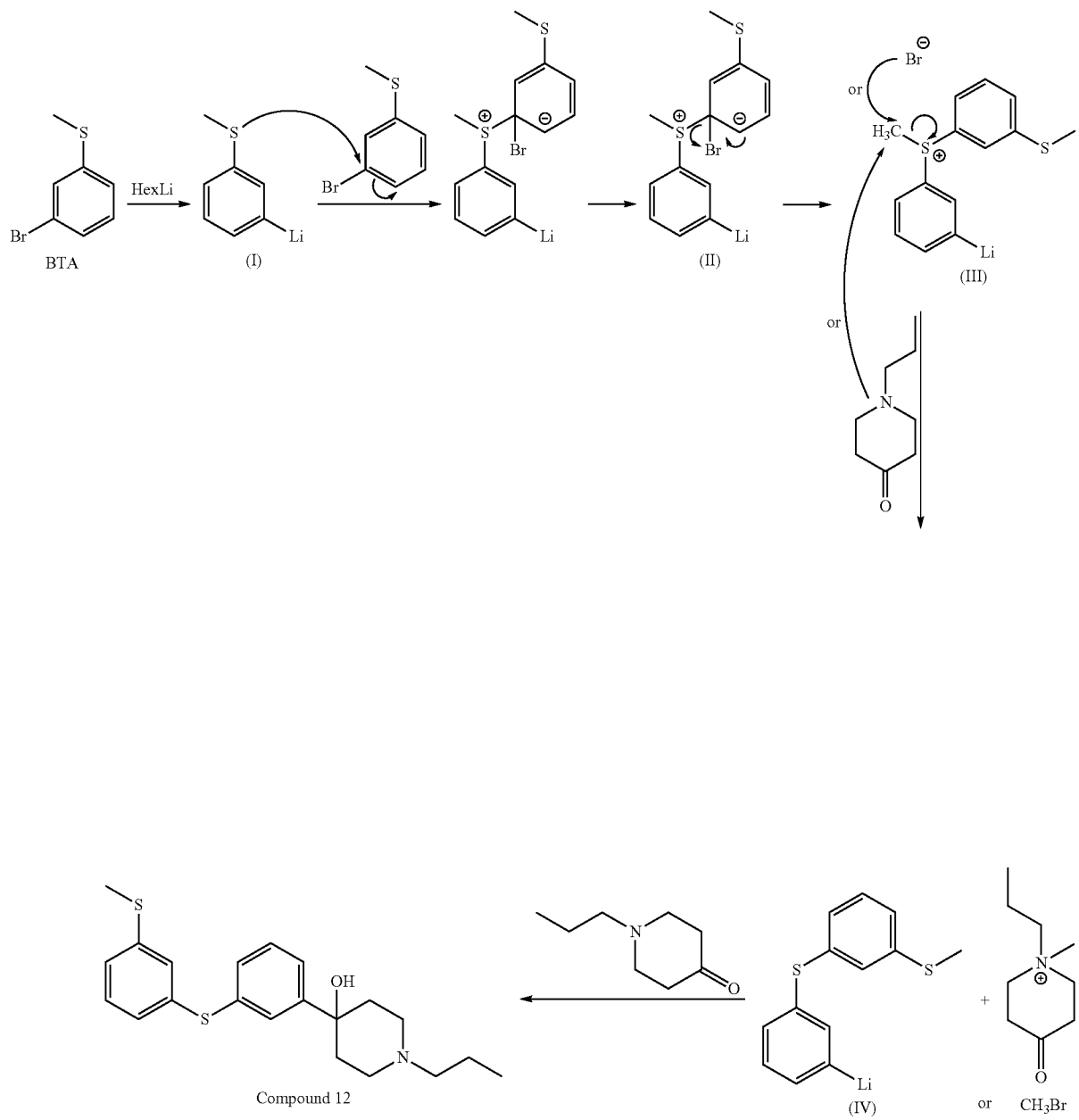

After understanding that formation of Compound 12 is related to excess of 3BTA over HexLi and that all the HexLi is in the reactor and 3BTA is added in portions over an extended period of time it was concluded that simultaneous addition of 3BTA and HexLi, or addition of HexLi to 3BTA (reverse addition) can be a solution for avoiding formation of high levels of Compound 12 during Compound 9 preparation.

BTA addition was complete, the reaction mixture could be kept for at least 8 h (entry 12 in Table 29).

Temperature During Lithiation

Reaction temperature was important as shown in entries 5, 6, 13, 15, 16 and 19 of Table 29. The level of Compound 12 or assay of Compound 9 were both undesirable when the reactions were conducted at −60° C. or −50° C. (entries 6, 13 and 15 in Table 29). When the temperature during

TABLE 29

Reverse addition, conditions and results summary

| Entry | BTA addition time (h) | HexLi eq. | Temp (° C.) | IPC1 (%) | RRT 0.84 in mother liquor (area-%) | RRT 0.84 in Compound 9 (area-%) | Compound 12 in mother liquor (area-%) | Compound 12 in isolated Compound 9 | Assay (%) | Yield (%) |
|---|---|---|---|---|---|---|---|---|---|---|
| 1 | 1 h 10 min | 1.07 | −74 | | 8.6 | 0 | <0.05 | 0.01 | n.d. | 60 |
| 2 | 18 h | 1.07 | −76 | | 13.5 | 0.09 | 0.05 | 0.06 | 97.7 | 67 |
| 3 | 18 h | 0.97 | −67 to −73 | 85.1 | 10 | 0.08 | 0 | 0.55 | 95.6 | 42 |
| 4 | 16 h | 1.07 | −70 to −76 | 99.1 | 6.7 | 0.07 | 0 | 0.16 | 98.0 | 69.1 |
| 5 | 4 h | 1.07 | −75 | | | | | 0.04 | | 64 |
| 6 | 4 h | 1.07 | −50 | | | | | 0.65 | 78.2 | 64 |
| 7 | 10 h, 1 h hold time, poor stirring | 1.07 | −70 to −55 | 79.4 | 17.5 | 0.52 | 0.15 | 2.13 | n.d. | 63 |
| 8 | 8 h | 0.89 | −76 to −80 | 82 | | 0.05 | | 0.13 | n.d. | 57 |
| 9 | 8 h, 2 h hold time | 1.07 | −78 to −80 | | 5.4 | | <0.05 | 0.15 | n.d. | 48 |
| 10 | 8 h | 1.07 | −84 to −60 | 95.6 | | 0.05 | | 0.07 | 99.2 | 70 |
| 11 | 8 h | 1.6 | −79 to −70 | 100 | | 0 | | 0 | 100.1 | 69 |
| 12 | 8 h, h8 hold time | 1.07 | −75 to −67 | 92.9 | 17 | 0.05 | 0 | 0.06 | 99.7 | 70 |
| 13 | 8 h | 1.08 | −60° C. | | 6.0 | 0 | 0.26 | 0.81 | n.d. | 55 |
| 14 | 8 h, Poor stirring | 1.07 | −79 to −75 | 64 | 6 | 0.05 | 0 | 0.17 | n.d. | 48 |
| 15 | 8 h, 8 h hold time | 1.2 | −60 | 86.8 | 17 | 0.07 | 0 | 1.12 | n.d. | 69 |
| 16 | HexLi/THF kept at −65° C. for 15.5 h, BTA added in 4.5 h | 1.2 | −65 | 96.3 | 13 | 0.07 | 0 | 0.13 | 97.5 | 70 |
| 17 | 9 h HexLi, 3.5 h hold time, 8 h BTA, 4 h hold time | 1.2 | −65 | 89.8 | | 0 | | 0.34 | 96.4 | 70 |
| 18 | 2 h HexLi, 2 hold time, 14 h BTA, 1 h hold time | 1.2 | −74 to −71 | 96.1 | 3.5 | 0.04 | 0 | 0.11 | 97.0 | 73 |

Addition Time and Holding Time After Addition

With the encouraging result achieved in the first experiment (entry 1 in Table 29), the following method development work was started by examining addition and post-reaction time of BTA. The results displayed in Table 29 and entries 1-5 showed that the addition time is not crucial as long as it is performed at temperature equal to or less than −70° C. However, hold time is crucial if it is kept at equal to or greater than −60° C. (for 8 h (entry 15 in Table 29) Compound 12 was increased dramatically). When the temperature was held at equal to or less than −70° C. after the lithiation was increased to −65° C., low levels of Compound 12 were achieved (entries 16-17 in Table 29). It is obvious that the system generates high levels of Compound 12 when running perpetually at −60° C. or above (entries 6, 13 and 15). However, a temporary temperature overshoot above −60° C. (could be happen due to exothermic precipitation of the lithiated species) is not an issue (entry 10 in Table 29). If a temperature overshoot takes place, the addition of BTA must be stopped and can only be resumed when the temperature in the content is below 70° C.

Stoichiometry of HexLi Against BTA

Since Compound 12 is formed when BTA is in excess, the stoichiometry of HexLi against BTA was studied. Four different mole equivalent of HexLi were examined 0.89, 1.07, 1.2 and 1.6 eq in entries 8, 4, 18 and 11 in Table 29, respectively and all experiments ended with the Compound 12 level within specification. A deficit of HexLi does not have significant impact on the formation of Compound 12 as long as the temperature is kept less than or equal to −70° C. during BTA addition (entries 3 and 8 in Table 29). A large excess of HexLi, 1.6 eq produced Compound 9 with 100% purity. This can be explained by the complete lithiation of BTA which lead to no unreacted BTA, which is needed for formation of Compound 12. However it did not give any significant difference in term of yield. Due to a decline in capacity and no improvement in yield, 1.6 eq HexLi was not selected. The other reason for not selecting 1.6 eq HexLi was based on the papers found in the literature (Shirley et al. Journal of Organometallic Chemistry 16 (1969) p. 1-6 and Cabiddu et al. Tetrahedron 60 (2004) 3915-3920) that described the risk for over-lithiation of BTA either on the aromatic system and/or on the methyl group of the thioanisole. 1.07 eq HexLi was the stoichiometry implemented in the 'normal addition mode' HexLi to BTA and was shown to give yield and quality within acceptable ranges (entries 4 and 11 in Table 29). However, based on the results achieved in entries 16-18 in Table 29, 1.2 eq HexLi was selected to be used further. This was selected based on balancing the excess of BTA, consumption of HexLi and process capacity.

The assays of Compound 9 materials obtained in laboratory are displayed in Table 29 and showed levels not less than 96%. The assay test does not have a limit currently.

In-Process Control

Since the latest experiments (entries 16-18) showed variation in in-process control values (87-96%) but the obtained Compound 9 of sufficient quality and yields that were consistently 69-73%, at a hold time of approximately 30-60 minutes after completion of HexLi addition is appropriate and in-process control can be excluded. It is also not relevant to perform any in-process control since no corrective action can be made at this stage. The major benefit in excluding in-process control sampling and analysis is that hold time, which is the most critical stage in the entire process can be controlled. The unreacted BTA is discarded in the organic layer in work-up.

Simultaneous Addition of 3BTA and HexLi in Batch Mode Related to Example 1

Another way to avoid excess of BTA in the lithiation reaction is to add BTA and HexLi simultaneously. One disadvantage is that the addition time would be longer because both BTA and HexLi require cooling in the lithiation reaction.

Two experiments have been carried out and the results that are summarized in Table 30 below are positive.

As can be seen from the results of these two experiments, the purity profile as well as yield are similar to the results achieved through reverse addition mode.

Conclusion

By changing the order of addition from normal addition to reverse addition i.e. addition of 3-bromothioanisole to hexyl lithium, the impurity Compound 12 is suppressed dramatically.

It is important to keep the temperature during lithiation≤−70° C. However temporary overshooting of temperature to ≤−60° C. is not an issue. The side reaction is enhanced slightly at −65° C. Lithiation at −60° C. has shown to give undesirable results regarding Compound 12.

The purity profile of Compound 9 obtained in the modified method of this Example is better than previous methods and contains only Compound 12 and Compound 16.

Addition time at lithiation stage is not critical and has been tested up to 18 h. The amount of HexLi is increased from 1.07 eq. to 1.2 eq. with no effect on the yield which remains at 70%.

Two experiments regarding simultaneous additions of BTA and HexLi during the lithiation reaction gave promising results. This approach is judged to be effective in suppressing Compound 12.

REFERENCES CITED

U.S. Pat. No. 6,903,120
U.S. Pat. No. 7,923,459
U.S. Publication No. US-2013-0267552-A1
CSID:25948790, http://www.chemspider.com/Chemical-Structure.25948790.html (accessed 23:27, Jul. 15, 2016).
CSID:7971505, http://www.chemspider.com/Chemical-Structure.7971505.html (accessed 23:33, Jul. 15, 2016).
Ebenezer et al, Tetrahedron Letters 55 (2014) 5323-5326.

The invention claimed is:

1. A process for preparing solid pridopidine base comprising
   a) obtaining a solution comprising pridopidine base,
   b) washing the solution comprising pridopidine base with water, and
   c) precipitating pridopidine base from the solution to form solid pridopidine base.
2. The process of claim 1 further comprising precipitating pridopidine base with a volume of one or more alkanes.
3. The process of claim 1,
   (a) wherein the solution comprises one or more organic solvents or water, or a mixture thereof,
   (b) wherein the solution is a mixture of toluene and water,
   (c) further comprising adding a strong base to the solution,
   (d) wherein the solution comprises an aqueous layer and an organic layer, and the process further comprises

TABLE 30

Simultaneous additions of BTA and HexLi, conditions and results

| Experiment No. | BTA & HexLi addition time + hold time (h) | HexLi eq. | Temp (° C.) | RRT 0.84 in mother liquor (area-%) | RRT 0.84 in Compound 9 (area-%) | Compound 12 in mother liquor (area-%) | Compound 12 in isolated Compound 9 | Yield (%) |
|---|---|---|---|---|---|---|---|---|
| 2809 | 8 h | 1.07 | −77 to −73 | 7.4 | 0.09 | 0 | 0.02 | 64 |
| 2810 | 4 h + 1 h | 1.07 | −75 | | | | <0.1 | 57 | separating the organic layer from the aqueous layer and washing the organic layer with water, or
(e) wherein the step of washing the organic layer with water removes Compound 1:

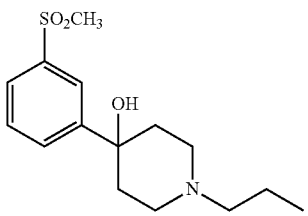

Compound 1 from the organic layer.

4. The process of claim 1, wherein the process further comprises
  (a) forming the pridopidine base with a chemical purity in which the weight percent of Compound 1 is less than 0.2% of the total amount of pridopidine base and Compound 4 and/or
  (b) removing an amount of the organic solvent under vacuum distillation to obtain a mixture comprising a volume of the organic solvent wherein the ratio of the volume of organic solvent to the volume of one or more alkanes during the step of precipitating the pridopidine base is between 1:1.3 to 1:3 and/or
  (c) precipitating pridopidine base after the vacuum distillation and forming the pridopidine base.

5. The process of claim 1, further comprising a catalytic reduction of the compound of Compound 8

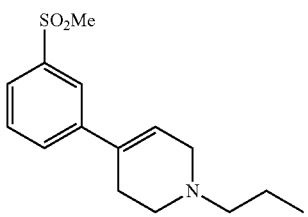

Compound 8 at a predetermined reduction temperature and with an amount of a reduction catalyst to form pridopidine base and wherein
  (a) the reduction catalyst is selected from the group consisting of a palladium catalyst, a platinum catalyst, a ruthenium catalyst, a palladium on carbon catalyst, and JM type 402 catalyst,
  (b) the amount of the reduction catalyst is 5%-20% w/w,
  (c) the catalytic reduction is complete in 0.1-20 hours
  (d) wherein the predetermined reduction temperature is 5-60° C.
  (e) the predetermined reduction temperature is 0-39° C. or
  (f) the pridopidine base formed is free of pridopidinium.

6. The process of claim 5, further comprising dissolving Compound 8 in water and mixing Compound 8 with a weak acid.

7. The process of claim 5, wherein the process further comprises cold addition of weak acid and reduction catalyst at a temperature between 9 and 21° C. before slowly warming the reaction mixture to a temperature between 20 and 30° C. to prevent the formation of pridopidinium.

8. The process of claim 1, further comprising oxidizing Compound 10:

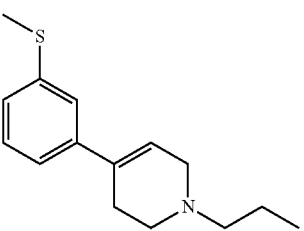

Compound 10 with a catalytic oxidizing agent and an oxidant; to give Compound 8:

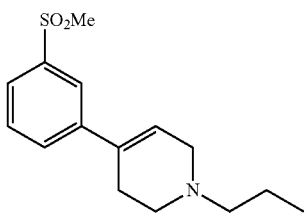

Compound 8 and wherein
  (a) the step of oxidizing Compound 10 is conducted at a temperature of 40-60° C.,
  (b) the catalytic oxidizing agent is a tungsten oxidizing agent, or
  (c) wherein the oxidant is a peroxide.

9. The process of claim 8, further comprising adding the oxidant in two batches, a first batch and a second batch.

10. The process of claim 1 further comprising dehydrating Compound 9:

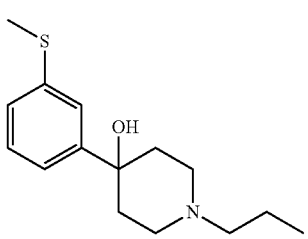

Compound 9 with a strong acid for an amount of time and at a temperature; to give Compound 10 or a solution comprising Compound 10 and wherein
  (a) the yield of the step of dehydrating Compound 9 is 20-95%,
  (b) wherein the amount of strong acid is 1.5-4.5 equivalents,
  (c) the amount of time is 1-22 hours,
  (d) wherein the temperature is below 118° C.,
  (e) the strong acid is sulfuric acid,
  (f) the dehydration of Compound 9 with a strong acid is conducted in solvent selected from toluene, xylene, or hexanes,
  (g) Compound 10 is extracted from the solution comprising Compound 10 using water and without the use of NaOH,

69

(h) the chemical purity of Compound 10 is 90-99.4%, or
(i) the yield of the step of dehydrating Compound 9 is 20-95%.

11. The process of claim 3, further comprising lithiating 3-bromothioanisole with an alkyllithium using a continuous flow reactor to obtain 3-lithium thioanisole.

12. The process of claim 11,
(a) wherein the continuous flow reactor comprises a solvent and wherein the solvent is THF,
(b) wherein lithiation of 3-bromothioanisole has an average residence time of 1-60 seconds,
(c) further comprising performing a coupling reaction between 3-lithium thioanisole and 1-propyl-4-piperidone to form Compound 9 or a solution comprising Compound 9 using a continuous flow reactor,
(d) wherein the coupling has an average residence time of 8-480 seconds,
(e) wherein the lithiation of 3-bromothioanisole and/or the coupling is performed at a temperature of between 15° C. and −100° C.,
(f) wherein the amount of equivalents of the lithiating agent used is between 0.97 and 1.20,
(g) wherein the lithiating agent is an alkyllithium,
(h) further comprising precipitating Compound 9 from the solution to form solid Compound 9,
(i) further comprising quenching the solution comprising Compound 9 with water to form a solution comprising a compound of Compound 9,
(j) further comprising adding toluene to the solution comprising Compound 9 and washing with water,
(k) further comprising distilling a solution comprising Compound 9 by vacuum distillation,
(l) wherein Compound 9 is precipitated with an alkane selected from pentane, hexane, heptane, and octane, or
(m) wherein the solution comprising Compound 9 or the solid Compound 9 is free of THF or THF residues.

13. The process of claim 1, further comprising lithiating 3-bromothioanisole with a lithiating agent followed by performing a coupling between 3-lithium thioanisole and 1-propyl-4-piperidone to form the hydrochloride salt of Compound 9 or a solution comprising the hydrochloride salt of Compound 9 and using a vacuum distillation to obtain a composition comprising the hydrochloride salt Compound 9 wherein the composition comprises less than 1% w/w.

14. A process for preparing pridopidine hydrochloride from pridopidine free base comprising
a) obtaining solid pridopidine free base,
b) dissolving solid pridopidine free base in an alcohol to form a solution,
c) filtering the solution, and
d) adding to the solution a mixture of hydrochloric acid and an alcohol which is the same as the alcohol in which the pridopidine base is dissolved in step (b) to precipitate pridopidine hydrochloride.

15. The process of claim 2, wherein the alkane is n-heptane.

16. The process of claim 3, wherein in step (c) the strong base is NaOH which is added until the pH of the solution is pH 11-14.

17. The process of claim 5, wherein
(a) the amount of the reduction catalyst is 8%-10% w/w,
(b) the catalyst is a JM type 402 catalyst,
(c), the catalytic reduction is complete in 0.5-1 hour, and/or
(d) the predetermined reduction temperature is 30-40° C.

70

18. The process of claim 8, wherein
(a) the step of oxidizing Compound 10 is conducted at a temperature of 35-55° C.
(b) the catalytic oxidizing agent is sodium tungstate dihydrate, and/or
(c) the oxidant is hydrogen peroxide.

19. The process of claim 10, wherein
(a) the yield of the step of dehydrating Compound 9 is about 95%,
(b) the amount of strong acid is 1.8-2.5 equivalents,
(c) the amount of time is about 3.5 hours,
(d) the temperature is between 57° C. and 80° C., and/or
(e) the chemical purity of Compound 10 is 98.9-99.4%.

20. The process of claim 12, wherein
(a) the lithiation of 3-bromothioanisole has an average residence time of 4-10 seconds,
(b) the coupling has an average residence time of 8-15 seconds,
(c) the lithiation of 3-bromothioanisole and/or the coupling is performed at a temperature of between −5° C. and 5° C.,
(d) the lithiating agent is Hex-Li,
(e) the Compound 9 formed is free of Compound 16

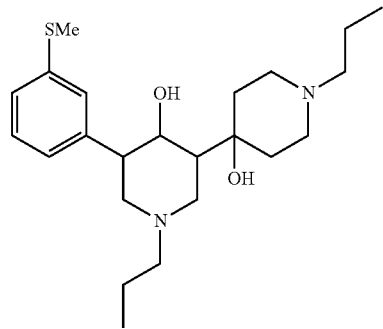

Compound 16

(f) the Compound 9 formed has a chemical purity with a THF level of 2-100 ppm, and/or
(g) Compound 9 is precipitated with heptane.

21. The process of claim 1, further comprising washing the pridopidine base formed in step c) with isopropyl alcohol.

22. The process of claim 9, further comprising adding the first batch of oxidant, followed by adding the second batch of oxidant after the accumulated heat of the exothermic oxidation from the addition of the first oxidant batch is released.

23. The process of claim 14,
(1) wherein the alcohol is isopropyl alcohol,
(2) wherein the pridopidine hydrochloride formed has less than 0.07% by weight of Compound 4, or
(3) further comprising the step of crystallizing the pridopidine hydrochloride.

24. A composition comprising:
(a) Compound 9 having an assay of more than 96.6%,
(b) Compound 9 having a chemical purity of more than 99.0%,
(c) wherein said composition is free of 3-bromothioanisole,
(d) wherein said composition is free of THF, chloride, hexylbromide; 1-chlorobutanol; or thioanisole, (e) a composition comprising Compound 9, wherein the composition is free of chloride,
(f) a composition comprising Compound 8, wherein the amount of Compound 11 present in the composition is less than 0.30% by weight or less than 0.15% by weight,
(g) a composition comprising Pridopidine HCl, wherein the amount of Compound 4 present in the composition is less than 0.15% by weight or less than 0.10% by weight,
(h) a composition comprising Compound 9, wherein the amount of Compound 12 present in the composition is less than 0.30% by weight, or
(i) a composition comprising pridopidine HCl, wherein the amount of Compound 13 present in the composition is less than 0.15% by weight.

* * * * *